US005741314A

United States Patent [19]
Daly et al.

[11] Patent Number: 5,741,314
[45] Date of Patent: Apr. 21, 1998

[54] EMBEDDED DATA LINK AND PROTOCOL

[76] Inventors: Christopher Newton Daly, 95 Cheryl Crescent, Bilgoa Plateau, NSW 2107; Hugh McDermott, 51 Neill Street, Carlton, Victoria 3053, both of Australia

[21] Appl. No.: 708,348

[22] Filed: Sep. 4, 1996

[30] Foreign Application Priority Data

Oct. 19, 1995 [WO] WIPO ............... PCT/AU95/00694

[51] Int. Cl.$^6$ ........................................... A61N 1/00
[52] U.S. Cl. ........................ 607/60; 607/55; 128/903
[58] Field of Search ..................... 607/55, 60; 128/903

[56] References Cited

U.S. PATENT DOCUMENTS 4,944,299  7/1990  Silvian .

FOREIGN PATENT DOCUMENTS

| | | |
|---|---|---|
| 3492589 | 5/1988 | Australia . |
| 145430 | 6/1985 | European Pat. Off. . |
| 179536 | 4/1986 | European Pat. Off. . |
| 200321 | 11/1986 | European Pat. Off. . |
| 200359 | 12/1986 | European Pat. Off. . |
| 214352 | 3/1987 | European Pat. Off. . |
| 425777 | 5/1991 | European Pat. Off. . |
| 493176 | 7/1992 | European Pat. Off. . |
| 522611 | 1/1993 | European Pat. Off. . |
| 4-298127 | 10/1992 | Japan . |
| 2258371 | 2/1993 | United Kingdom . |
| 82 00203 | 9/1982 | WIPO . |
| 92 06160 | 7/1992 | WIPO . |

OTHER PUBLICATIONS

Theoretical Design and Implementation of a Transcutaneous, Multichannel Stimulator for Neural Prosthesis Applications; by Ian C. Forster; BIO–ENG 80 Conference, London, Mar. 23–26, 1980.

PCT International Search Report, International Application No. PCT/AU95/00694, Filing Date: Oct. 19, 1995.

Article — "Transmission Reception Circuit for Induction Radio Equipment" — No. 298127 — Oct. 21, '92.

*Primary Examiner*—Scott M. Getzow
*Attorney, Agent, or Firm*—Gottlieb, Rackman & Reisman

[57] ABSTRACT

A data link and protocol for a subcutaneous, tissue stimulating device. While stimulation is taking place, under control of pulses whose durations in a data frame determine the stimulation pulse widths, data is actually transmitted and processed for determining the parameters of the next stimulation. Thus transmission of data occurs simultaneously with stimulation. Data is represented by sequences which have more 1s than 0s, with each 1 being represent by a number of successive RF cycles and a single 0 by the absence of a number of RF cycles. In this way a duty cycle of 75% can be achieved so that required power is transferred to the implant. Variations in link condition, e.g., degree of ringing, are accommodated by means of offset tuning the transcutaneous transmit and receive coils. This ensures that the oscillating signal in the receive circuit that persists during the transmission of a 0 becomes out-of-phase with the RF transmission that is received for the next 1. The signal induced in the receive coil with the transmission of a new 1 cancels the out-of-phase ringing in the receive coil due to the earlier transmission, thereby causing the oscillation's amplitude to fall below a detection level to ensure the detection of an earlier transmitted 0 during the time that the next 1 is transmitted. A bit decoder is implemented that unambiguously recovers the number of 1s over a prescribed range of link transmission conditions.

73 Claims, 15 Drawing Sheets

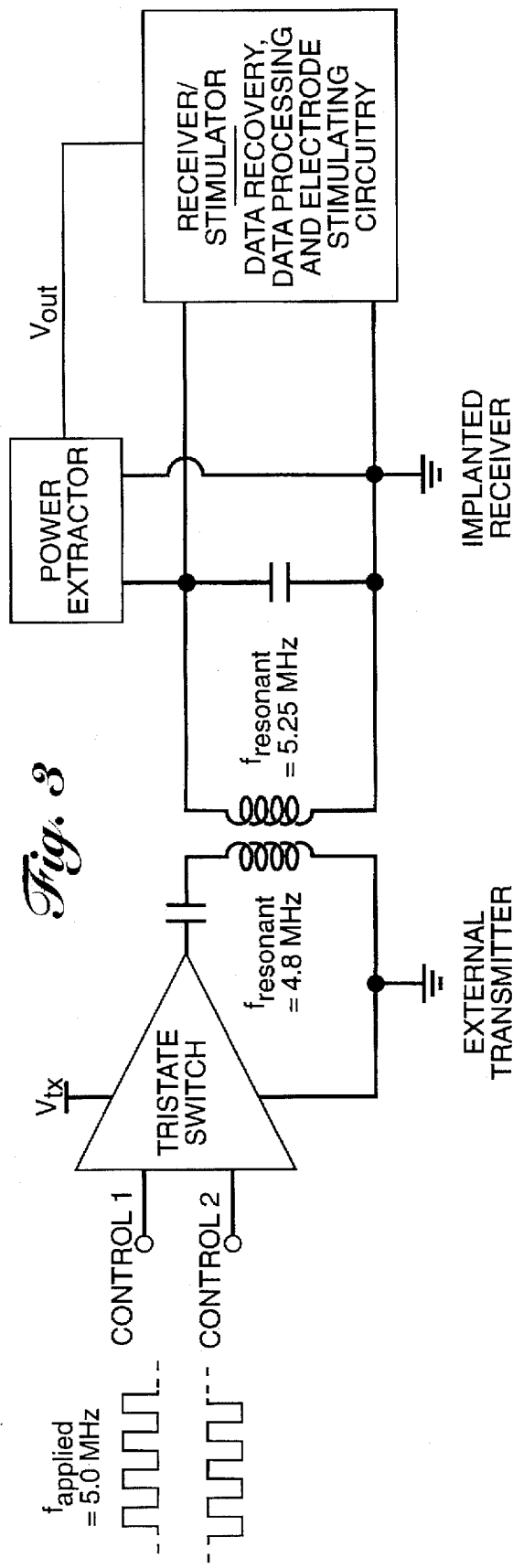

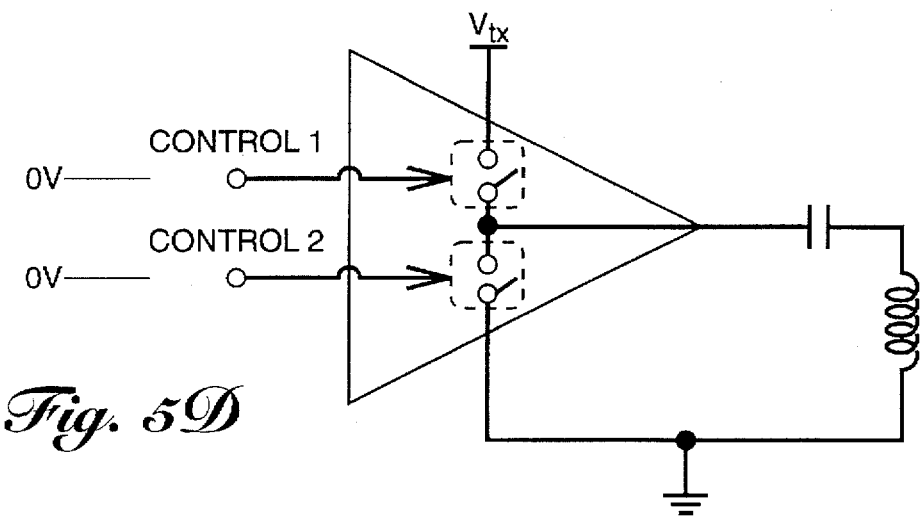
*Fig. 5D*
*Fig. 6A*
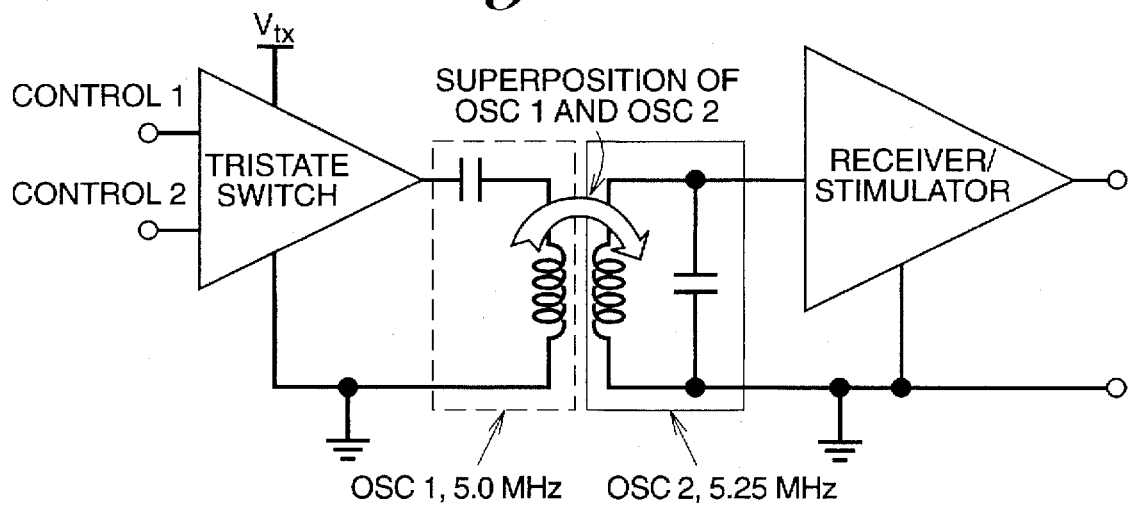
*Fig. 6B*
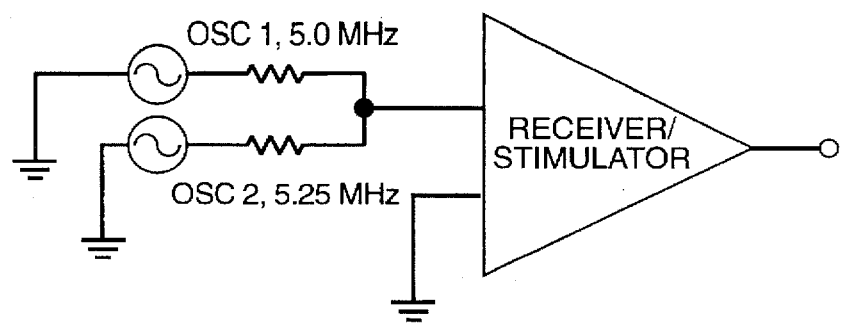

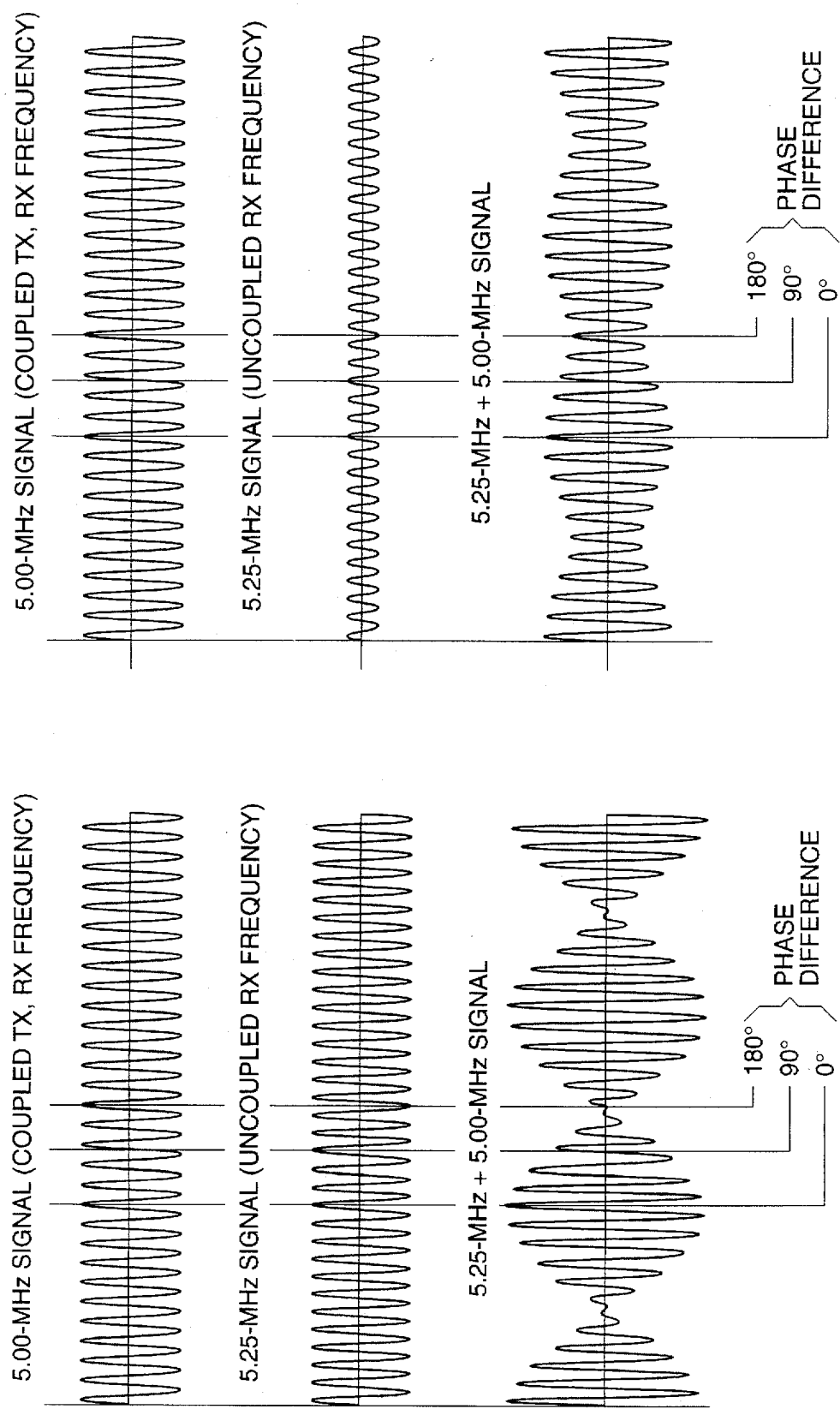

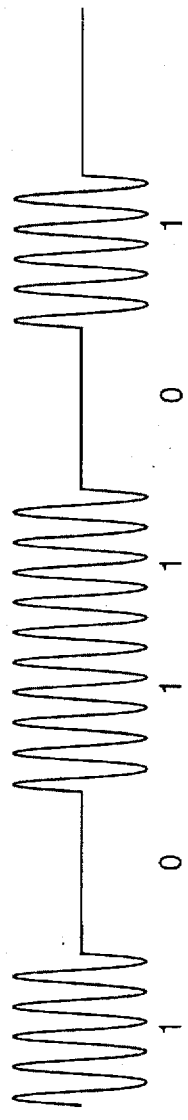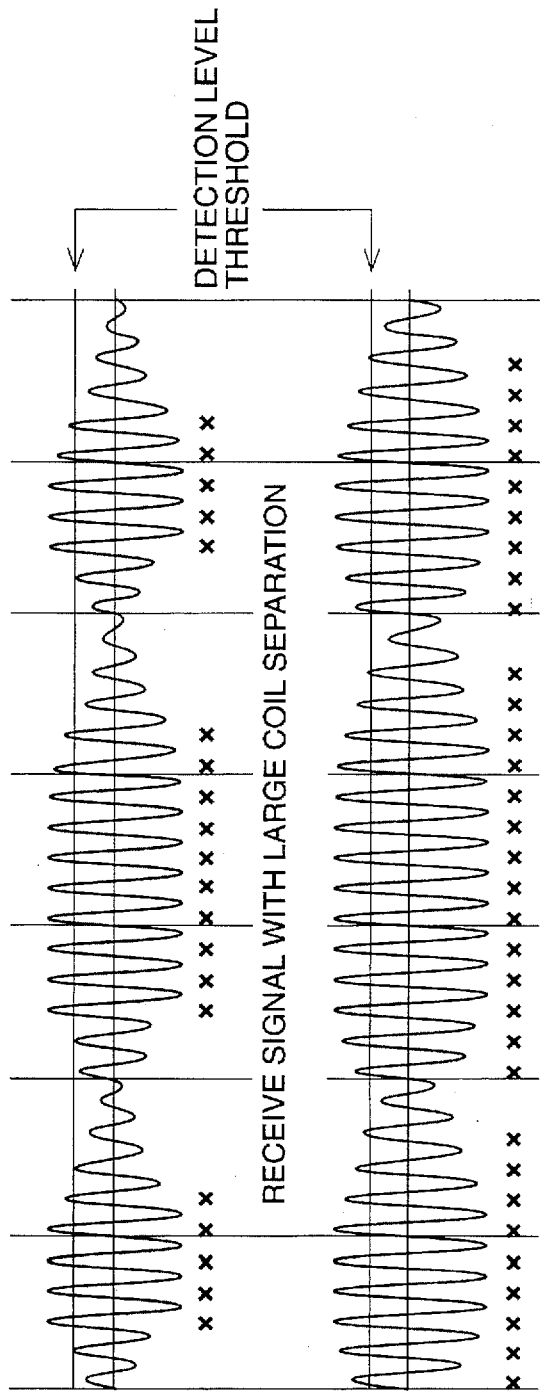

FOR A FIXED DETECTION THRESHOLD THE NUMBER OF DETECTED CYCLES VARIES AS THE COUPLING BETWEEN THE COILS IS ALTERED.

| Token No. | Token | Tri-Bit Represented | Parity |
|---|---|---|---|
| 1 | 101010 | Sync Ph1 | |
| 2 | 101011 | Sync Ph2 | |
| 3 | 101101 | 011 (Even Parity Error Token) | 0 |
| 4 | 101110 | 000 | 0 |
| 5 | 101111 | 001 | 1 |
| 6 | 110101 | Discarded | |
| 7 | 110110 | 101 | 0 |
| 8 | 110111 | 010 | 1 |
| 9 | 111010 | Discarded | |
| 10 | 111011 | 110 | 0 |
| 11 | 111101 | 111 (Odd Parity Error Token) | 1 |
| 12 | 111110 | 100 | 1 |

6 - CELL DATA TOKEN ENCODING 3 BITS OF DATA

6 - CELL DATA TOKEN
ENCODING 3 BITS OF DATA

Fig. 16A

| ORIGINAL TOKEN | ERROR AFFECTED TOKEN |
|---|---|
| (a) 111110 | 101110 (f)<br>110110 (h)<br>111010 |
| (b) 111101 | 101101 (g)<br>110101 |
| (c) 111011 | 101011 SYNC PH2<br>111010 |
| (d) 110111 | 110101<br>110110 (h) |
| (e) 101111 | 101110 (f)<br>101101 (g)<br>101011 SYNC PH2 |
| (f) 101110 | 101010 SYNC PH2<br>111110 (a)<br>101111 (e) |
| (g) 101101 | 111101 (b)<br>101111 (e) |
| (h) 110110 | 111110 (a)<br>110111 (d) |

Fig. 16B

| | a | b | c | d | e | f | g | h |
|---|---|---|---|---|---|---|---|---|
| a | ░ | | | | | ✓ | | ✓ |
| b | | ░ | | | | | ✓ | |
| c | | | ░ | | | | | |
| d | | | | ░ | | | | ✓ |
| e | | | | | ░ | ✓ | ✓ | |
| f | ✓ | | | | ✓ | ░ | | |
| g | | ✓ | | | ✓ | | ░ | |
| h | ✓ | | | ✓ | | | | ░ |

(rows = RESULTANT TOKEN, columns = ORIGINAL TOKEN)

EMBEDDED DATA LINK AND PROTOCOL

This invention relates to data links and transmission protocols, and more particularly to the transmission of power and data to a tissue stimulating prosthesis such as a cochlear implant.

A current state-of-the-art cochlear implant hearing prosthesis consists of an in-the-body receiver/stimulator (RS) connected to an electrode array which is disposed along the auditory nerve. A wearable speech processor (WSP), containing a microphone and power source, is worn by the patient The WSP processes speech and transmits both power and data to the RS to control appropriate energizations of the electrodes.

The most widespread transmission system used for cochlear implants is disclosed in Crosby et al. U.S. Pat. No. 4,532,930, which patent is hereby incorporated by reference both for its discussion of the prior art in general and its depiction of a basic cochlear implant design that is by now being used by many thousands of patients. The data transmission format of the Crosby et al. system is shown in FIG. 2, this drawing being based on FIG. 8, of the aforesaid patent. Both power and data are transmitted in the form of an amplitude modulated RF signal, giving rise to six pulse bursts. The first burst is for synchronization purposes. The number of pulses in the second burst represents the active electrode, and the number of pulses in the third burst specifies the mode of operation. The second burst simply identifies one of twenty-two electrodes. The third burst, representing the mode, defines whether the stimulation should be bipolar or common ground, as well as a specific electrode number to be used as a reference if the stimulation is to be bipolar.

The fourth burst represents the amplitude of the stimulation. The second, third and fourth bursts convey digital information—the pulses in each burst are counted in order to derive the data under consideration.

The fifth and sixth bursts are analog in nature. Instead of counting the number of pulses in each of these bursts and deriving a digital number which represents the quantification of some parameter, it is the duration of each of the last two phases that directly controls how long a positive pulse is first applied and then how long a negative pulse is applied.

There are numerous considerations which go into the design of a data link and transmission protocol for a cochlear prosthesis. It is apparent that the higher the carrier frequency, the higher the potential data rate—the more RF cycles that can be transmitted in any unit of time, the greater the number of permutations of which cycles can be present and which can be missing, thus allowing the imparting of a greater amount of information. But there is a fundamental limitation on the maximum RF carrier frequency that can be used. The higher the frequency, the greater the losses in the transmitter. The transmitter includes a battery, and, due to the limited energy capacity of portable batteries, inefficient circuit design is to be avoided. In general, the higher the switching rate of a transistor, the greater the losses. Thus, while a high data rate is desired in order to stimulate the electrodes as rapidly as possible, the desire is to achieve this with a relatively low carrier frequency.

A major limitation on the data rate, and this applies to any carrier frequency, has to do with the duty cycle. Power can be transmitted to the implant only when cycles are present, not when they are missing. The ratio of the time when transmission is present to the time when it is not is called the duty cycle, and the higher the duty cycle, the greater the level of power which can be transferred from the transmitter section of the WSP to the receiver section of The RS. But the higher the duty cycle, the less flexibility there is in choosing whether cycles should be present or not. In other words, the higher the duty cycle, the lower the data rate. This problem affects amplitude modulation and on-off-keying modulation schemes. It is true that frequency modulated signals do not suffer from this problem, but they have two significant problems that make them unsuited for use with a cochlear implant device. First, the FM carrier is present all the time, even when no data is being transmitted, and this places an inordinate drain on a lightweight battery-powered transmitter. Second, both the transmitter and the receiver are more complex to implement, and this implies a higher component count, also a disadvantage in the environment of a cochlear implant.

There is also a basic problem in using the prior art amplitude modulation approach. The energy stored in a parallel tuned circuit takes a finite time to dissipate. The energy circulates between the coil and the capacitor, and the net energy reduces as a result of losses in the circuit. These losses can be expressed as the Q of the circuit (high Q meaning low losses). Typically it takes $Q/\pi$ cycles for the amplitude of the circulating current to reduce to a value of 1/e of its initial value. If the Q of the tuned circuit is 30–50, it can take more than 10 cycles for the current to build up or decay to a level at which detection is reliable. If each burst represents a bit of one value and the cessation of transmission represents a bit of the opposite value, and if it takes 10 cycles for a burst to build up or decay, it is apparent that the data rate can be only 5% of the RF carrier frequency. In general, it is very difficult to design a system in which the bit rate is more than 10% of the carrier frequency. And a straightforward design of this type, in which it is assumed that on average there are as many bits of one value as the other, gives rise to a duty cycle of only 50%, while typically higher duty cycles are desired in order to transfer as much power as possible to the implant. Straightforward binary encoding schemes do not produce optimal results.

Other approaches have their own limitations. For example, frequency shift keying and phase modulation techniques are considerably more complex to implement.

A particular shortcoming of the Crosby et al. approach discussed above is that each frame consists of two totally distinct parts. The first four bursts (sync, active electrode, mode and amplitude) basically set up the stimulus parameters for the implant, but convey no information about the durations of the two phases of stimulation. The durations of the two halves of each bi-phasic waveform are controlled by the actual widths of the last two bursts in the frame. It would be possible to transmit much more data if the bulk of each frame were devoted to representing the pulse durations, rather than to require a substantial part of each frame being used solely for set-up purposes.

BRIEF DESCRIPTION OF THE INVENTION

It is an object of the invention to provide a data link and transmission protocol which allow a high data rate for even a relatively low RF carrier frequency, without requiring complex circuitry or inefficient use of the power source.

It is another object of the invention to provide the aforesaid high data rate while achieving a duty cycle as high as 75%.

It is another object of the invention to provide a data link and transmission protocol in which the data is embedded in RF pulse bursts which represent stimulation durations, thus effectively prescribing the set-up of each bi-phasic stimulation simultaneously with the transmission of duration information and without requiring any substantial additional transmission time for it.

It is another object of the invention to provide a data link and transmission protocol which achieve the aforesaid objectives while being self-clocking, thus avoiding circuit complexity in that the received RF cycle sequence itself is all that is required for proper decoding.

In systems such as the aforesaid Crosby et al. system, cycles are counted. But each pulse does not represent a single increment. For example, for every 8N cycles detected by the receiver, a count of N might be registered. The transmitter sends 8N+4 cycles to ensure that at least 8N cycles are received. A divide-by-8 circuit is used in the decoder so that any number of received cycles between 8N and 8N+7, for example, will be decoded as N. A counting scheme such as this is simple to implement in CMOS circuitry, independent of a clock frequency as the logic operates at the carrier frequency. It is due to the slow build up and slow decay of a pulse burst in the receiving coil that perfect counting is not possible. That is why 8 cycles are transmitted for each count increment, and the offset of 4 cycles typically results in the number of decoded cycles falling inside the range from 8N to 8N+7 which is decoded as N.

This general principle is employed in the subject invention, although there are a myriad of differences between the Crosby et al. implementation and that of the subject invention. But the basic design choice is to count receiver circuit cycles rather than to rely on a more conventional amplitude modulation envelope detection scheme which, especially at high frequencies, is wasteful of transmitter power.

It is basically the absence of a single 0 "cell" between successive 1 "cells" that clocks the system, although the meaning of a "cell" will not be described until later. For the present, it is sufficient to understand that a cell consists of a predetermined number of successive RF cycles, or a predetermined number of missing RF cycles, with a 0 cell being detected if even a single RF cycle is missing. One of the unique features of the invention is that it is the transmission of a 1 cell (a predetermined number of successive RF cycles) that actually forces the ringing current in the receiver coil to fall between two threshold levels so that at least one RF pulse is sensed to be missing, reliable detection of a 0 cell thus actually being accomplished by the transmission of a succeeding 1 cell.

The invention also contemplates that as the coupling between the transmitter and receiver coils varies, the interaction between the oscillating energy in the two coils varies; as a consequence, the depth of the nulling of the energy that occurs in the receiver coil varies, resulting in a variable number of cycles whose amplitude will be above a fixed detection level. Typically, the separation between the coils in a cochlear implant application may be between 2 and 10 mm. Despite the unpredictability in the replication of the transmitted signal in the receiver coil (a 0 cell, which consists of a number of missing RF cycles between two successive 1 cells, can actually be detected by the amplitude of a single one of its constituent RF cycles falling below a data threshold in the receiver detection circuit), there is no need to provide a separate clock in the receiver and the decoding is based solely on the counting of carrier cycles.

There are two kinds of coding in the subject invention. The first pertains to the transmission of what are termed "cells". A cell of value 1 is represented by N successive cycles of an RF carrier frequency, and a cell of value 0 is represented by the suppression of RF transmission of a number (usually also N) of successive cycles. Although each cell truly represents one value or the other, the 0 and 1 bits represented by the cells are not the ultimate data. Six cells represent three ultimate data bits. The transmission of six bits would ordinarily allow 64 different permutations. However, far fewer permutations are allowed in order to maintain a 75% duty cycle. That is why the only 6-bit codes which are allowed represent far fewer than 64 possibilities. In fact, only 8 possibilities are represented by the three bits into which each set of 6 cells is translated. Thus, it must always be borne in mind that when reference is made to a bit value, it can be either to the value of a cell (N RF cycles or the suppression of N RF cycles), or an ultimate data bit representing information sought to be conveyed.

The RF cycles in the receiver coil are counted using a method that takes into account the likely range of effects due to coil interaction (e.g., inter-coil coupling and variation in Q of receive and transmit coils), and the number of cycles N of RF carrier used to represent a cell of value 1. At most one 0 cell is transmitted between successive 1 cells.

The receiver coil is tuned to a frequency offset from that of the transmitter coil. During the time that a 0 cell is transmitted (i.e., by preventing transmission of RF carrier cycles), the signal in the receiver coil changes phase relative to the phase of transmitted RF carrier. It must be understood that the phase of the RF carrier remains constant whether its transmission by the coil is allowed or is suppressed. The subsequent receipt of RF cycles representing a 1 cell causes at least one cycle of the RF signal in the receiver coil to fall below a detection threshold level by means of the out-of-phase interaction of the newly transmitted RF with the already present ringing in the receive circuit. The falling below detection level of the receive circuit oscillation represents the previously transmitted 0 cell. Thus, it is actually the transmission of a 1 cell after a 0 cell that forces the detection of the 0 cell.

With respect to the second coding level, in general terms it is well known that X successive bits may represent $2^X$ permutations. Thus, 6 successive bits or cells could theoretically represent $2^6$ or 64 permutations. But a subset substantially less than this number is allowed, each 6-bit member in this subset being called a "token". The token values selected are predominantly those with the fewest 0 bits. This allows the highest overall duty cycles and the transmission of maximum power to the implant. In general, each X-bit token represents only Y bit values, where Y is less than X, and the Y bit values constitute the ultimate information to be communicated external to the transmission system. (By "external" is meant the highest-level information generated by the WSP and actually required by the RS to control electrode stimulations.)

An important aspect of the subject invention is the way in which set-up data is actually embedded in the phase duration information. Each frame consists of two RF cycle sequences, each representing the duration of one of a biphasic pulse's phases, as in the Crosby et al. prior art. The difference is that there is no separate set-up data which is first sent in the subject invention. The set-up data, representing electrode, mode and amplitude, is actually transmitted as part of the two pulse bursts representing phase durations. It is apparent, however, that this presents an anomaly since duration information would necessarily be transmitted before electrode identification is even complete. For this reason, what is done is to transmit set-up data for the next frame while phase duration information is being transmitted for the present frame. Data is embedded in the phase duration pulse bursts, and this data is used to select the electrode, mode and amplitude of the next stimulation (whose biphasic durations will be transmitted in the next frame). This is the meaning of the term "embedded data link" in the title of the invention.

BRIEF DESCRIPTION OF THE DRAWINGS

Further objects, features and advantages of the invention will become apparent upon consideration of the following detailed description in conjunction with the drawings in which:

FIG. 3 depicts in general form the offset tuning of the transmitter and receiver coils in accordance with the principles of the subject invention;

FIGS. 5A–5D illustrate the four switch combinations in the tristate switch of the invention, and their effect on the transmitter tuned circuit;

FIGS. 6A and 6B illustrate a means of analyzing the coil interaction by treating the coils as oscillators and using a steady-state model to aid in visualizing the interaction between the two signals in the two coils;

FIGS. 7A and 7B respectively illustrate the effect of varying the amplitude of the signal generated by one of the oscillators in the steady-state model circuit of FIG. 6B.

FIGS. 9A and 9B show a transmitted waveform and corresponding signal induced in the receiver coil for two cases of inter-coil separation.

FIG. 15 is a chart that represents the maximum stimulation rate under certain conditions;

FIGS. 16A and 16B illustrate certain tokens and a token error matrix from which it will become apparent why particular tokens have been selected for use.

DETAILED DESCRIPTION OF THE INVENTION

Figure 1:
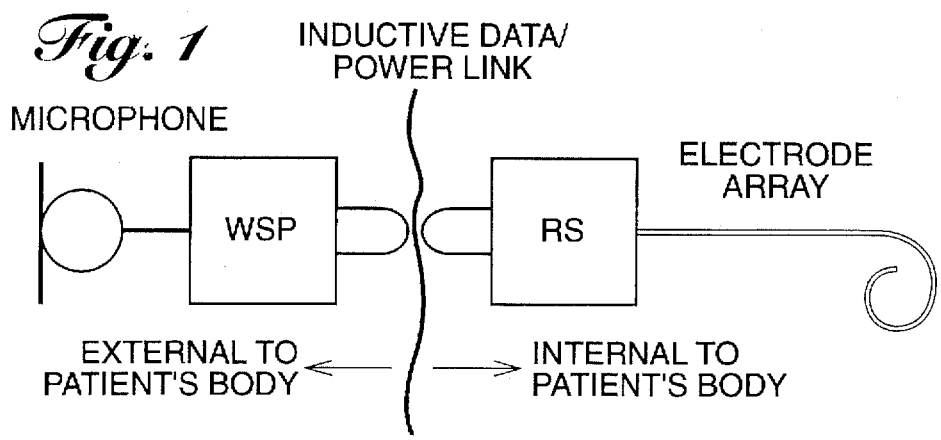
FIG. 1 is a block diagram of the two components of a cochlear prosthesis.

FIG. 1 depicts the overall configuration of a cochlear prosthesis. The patient carries a wearable speech processor (WSP) that includes a microphone and battery. Sound picked up by the microphone is analyzed to determine the best scheme of activating the electrode array in order to stimulate the auditory nerve so as to give the patient the most realistic perception of the sound incoming to the microphone. The stimulation scheme is converted to an RF signal which is applied to a transmit coil. A receive coil implanted in the patient's head picks up the RF transmission for processing by the receiver/stimulator (RS). The inductive link serves to transmit both data and power to the RS inside the patient's body. Extending from the RS is an electrode array which is inserted into the cochlea to allow stimulation of the auditory nerve.

Each stimulation consists of a biphasic, rectangular current pulse. The amplitude of the stimulation may be varied, and the parameter specifying the amplitude is denoted as A. The starting electrode from which the stimulation is to emanate is selectable, and this parameter is denoted as E. The reference electrode to be used as ground is also selectable, although all of the other electrodes can be used rather than just one. In general, the reference electrode(s), referred to as the mode, is denoted by M.

The fourth piece of information required for each biphasic stimulation is the duration of each phase. (In general, while the positive and negative phases usually have the same durations, they need not be equal.)

Figure 2:
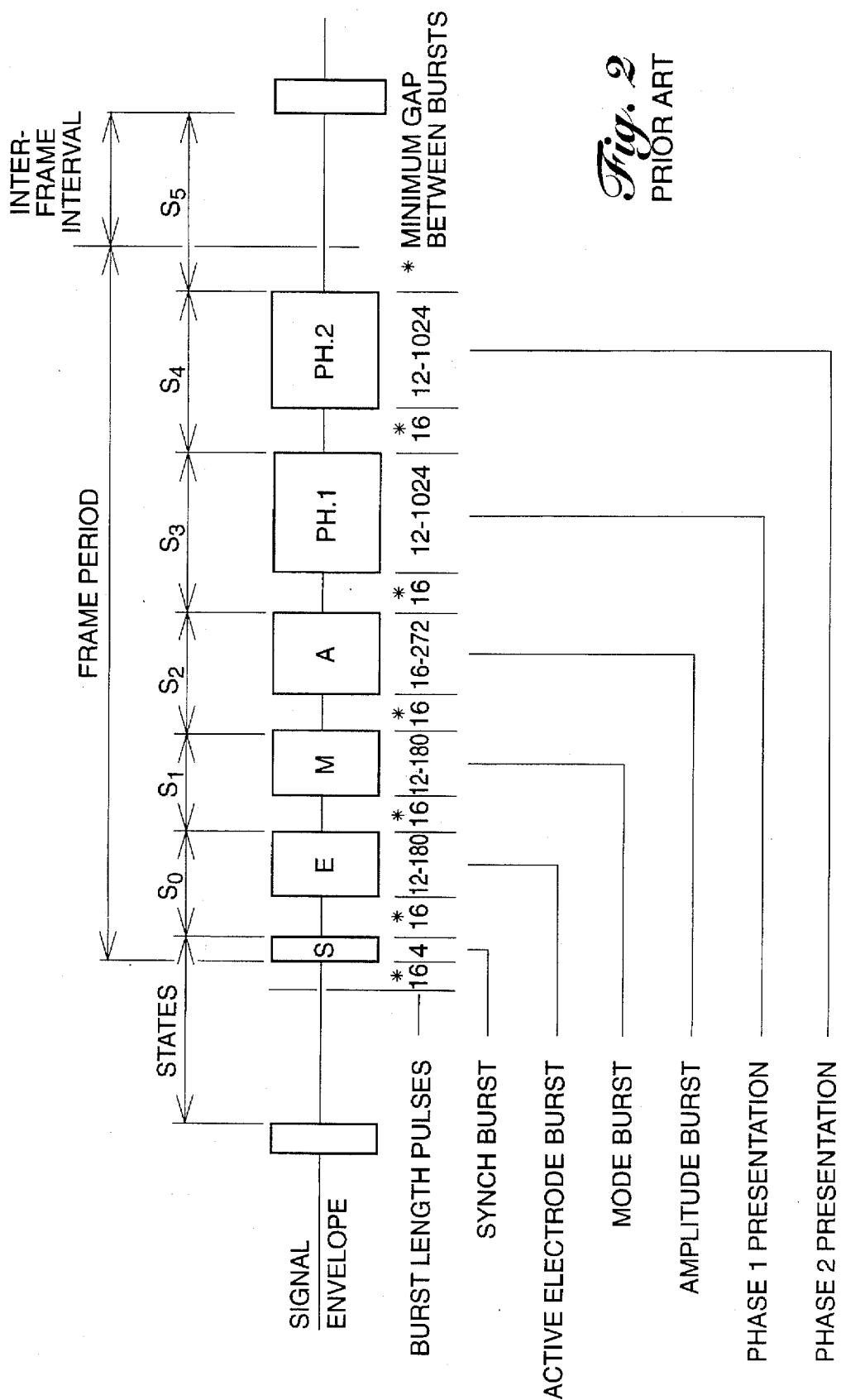
FIG. 2 depicts the transmission format of the prior art, as disclosed in Crosby et al. U.S. Pat. No. 4,532,930.

As discussed above, FIG. 2 depicts the transmission format of the cochlear implant which currently enjoys the most widespread use. Amplitude modulation is used, with the drawing depicting the signal envelope. The symbols $S_0$ through $S_5$ represent the system states. Typically, transmission ceases for 16 cycles between successive bursts, with the interframe interval being longer. The sync burst consists of only 4 pulses. The durations of the E, M and A states are shown in the drawing. As discussed above, the number of pulses in each burst represents quantitative information, and from this information the active electrode is selected, the mode is determined, and the current amplitude is set. At the end of the frame there are two bursts referred to as Phase 1 and Phase 2, and the duration of each represents the duration of a respective one of the two pulses in each biphasic pair. The general object of the subject invention is to transmit the same kind of information that is transmitted using the "SEMA" protocol, but with a much higher data rate, i.e., a much shorter frame period, without introducing any major complexities in the circuitry and at the same time achieving a duty cycle of about 75% in order to maximize the transfer of power to the implant. (A duty cycle of 75% means that the transmitter will be driving the series tuned transmit circuit for an average of 75% of the total duration of a data block. Duty cycle does not have to be maintained between data frames or blocks as implant power consumption is extremely low at those times.)

All of this is achieved with the use of a carrier frequency of 5.0 MHz, a frequency which allows relatively slow switching of transistors in the WSP so that there is minimal energy dissipation.

A circuit diagram of the inductive link used in the illustrative embodiment of the invention is shown in FIG. 3. The link consists of two resonantly tuned circuits separated by a distance that may be varied between approximately 2 mm and 10 mm. Variation in the distance between the two coils will affect the efficiency with which energy is coupled from the transmit circuit to the receive circuit. An important feature of the invention is that the two circuits are tuned to different resonant frequencies (for a reason to become apparent below), with an average frequency of about 5 MHz. This is the frequency at which the tristate switch is driven, by applying control signals to the two control inputs of the switch.

Figure 4:
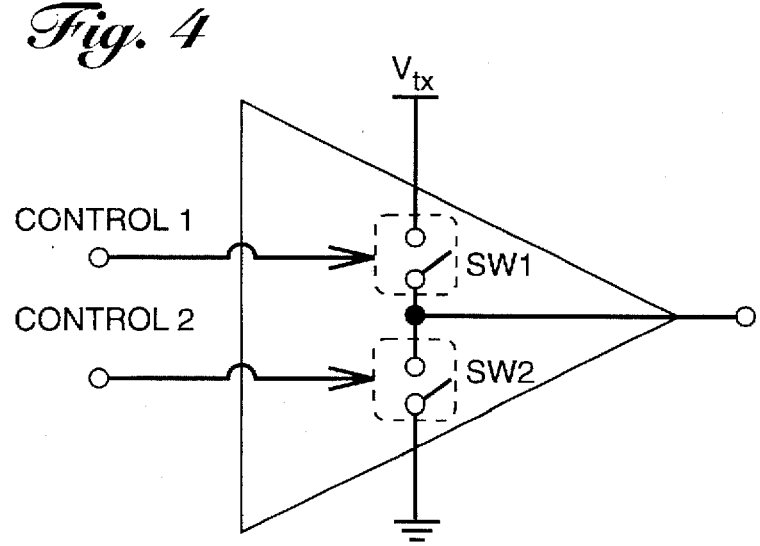
FIG. 4 is a block diagram depicting the inner workings of the tristate switch block shown in FIG. 3.

Operation of the tristate switch itself is shown in greater detail in FIG. 4. The device contains two switches SW1 and SW2, whose openings and closings are controlled by voltages applied to terminals labelled Control 1 and Control 2. Application of 0 volts will cause a switch to open, and application of $V_c$, typically 5 volts, will cause it to close. The two switches in the tristate switch are connected in series so that switch SW1 has a contact connected to supply voltage $V_{tx}$ which is a constant DC voltage, and switch SW2 has a contact connected to ground. The output of the tristate switch is connected to a point between the two switches.

Various combinations of control voltages applied to the Control 1 and Control 2 terminals of the switch will generate different outputs and the four possibilities are shown in FIGS. 5A–5D. These four figures show how the tristate switch can be used to charge and discharge the transmit LC circuit. If the switches SW1 and SW2 open and close fast enough, by application of the 5.0 MHz control signals shown in FIG. 5C, then an oscillation will be induced in the transmit circuit.

Figure 5A:
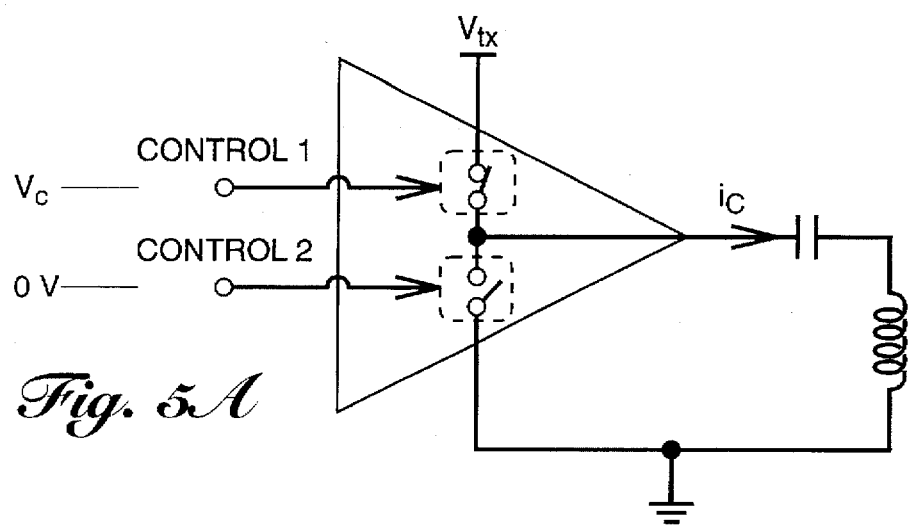
Figure 5B:
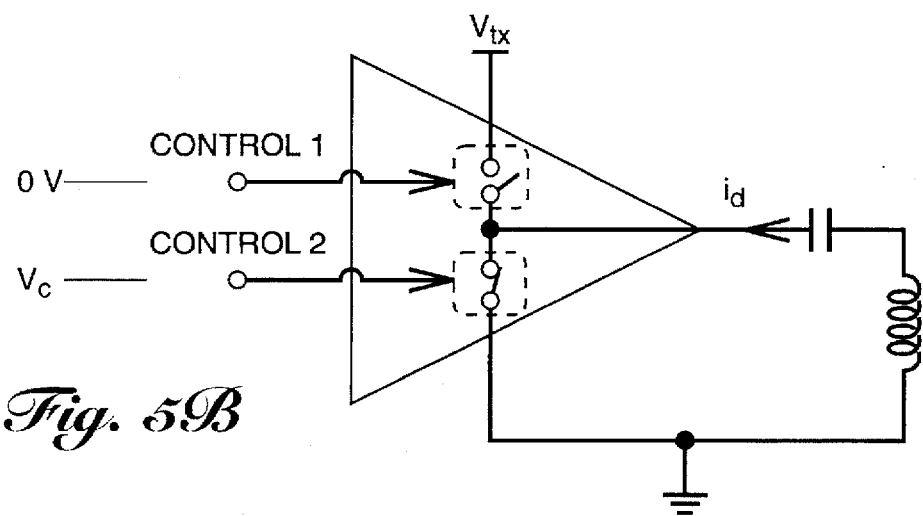

Application of $V_c$ to the Control 1 input while 0 volts are applied to the Control 2 input results in only the upper switch in the tristate switch closing. The voltage source $V_{tx}$ causes a charging current $i_c$ to flow through the circuit as shown in FIG. 5A. During the discharge cycle of FIG. 5B, with the lower switch closed rather than the upper, a discharge current $i_d$ flows in the opposite direction.

Figure 5C:
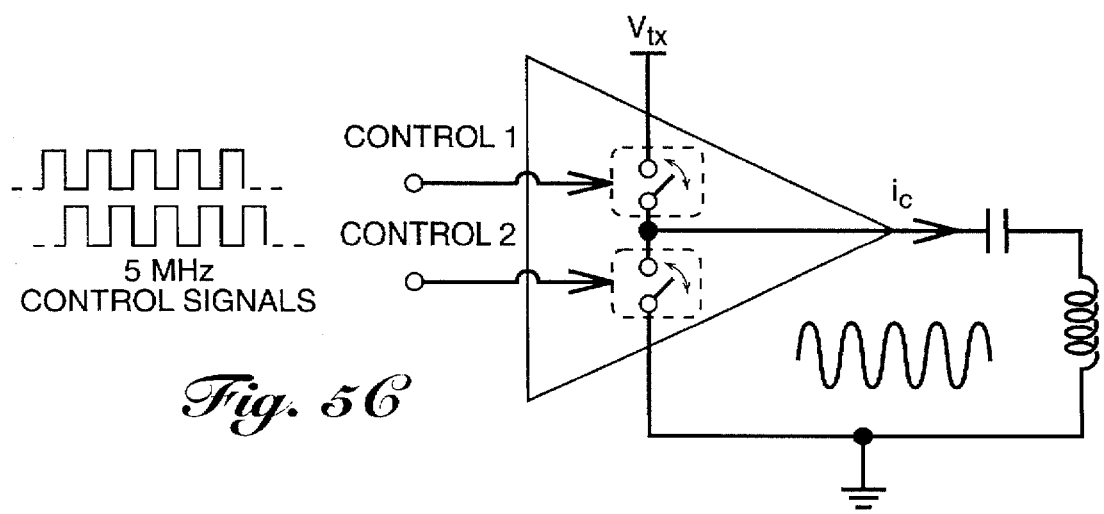

The way in which a 5.0-MHz oscillation is set up in the circuit is simply to apply out-of-phase 5.0-MHz control signals to the two control inputs. This forces alternate charge and discharge cycles, with the states represented in FIGS. 5A and 5B alternating, and with the result that there is a 5.0-MHz oscillating current in the circuit as shown in FIG. 5C. FIG. 5D shows the fourth possibility, with both of the control inputs at 0 volts and with no current flowing in the transmit circuit. The LC circuit is in effect disconnected from the transmit circuitry.

Application of the 5.0-MHz control signals forces the transmit circuit to resonate at 5.0-MHz. Energy is coupled across the link and induces a 5.0-MHz circulating current in the receive circuit. This is shown in FIG. 6A, with the transmit current being a 5.0-MHz circulating signal, referred to as Osc 1.

If 0 volts are now applied to each of the Control 1 and Control 2 inputs as shown in FIG. 5D, then the circulating current in the transmit circuit ceases abruptly and the two coils are no longer coupled. Decoupling of the two coils allows the energy in the receive circuit to begin oscillating at the circuit's natural resonant frequency of 5.25 MHz. There is now a gradual decaying oscillation in the receive circuitry, but it is at 5.25 MHz, not at 5.0 MHz.

When the 5.0 MHz control voltages are again applied as shown in FIG. 5C, a 5.0-MHz signal will be induced in the receive circuit. Without specifying the time at which the transmit circuit is re-energized, all that can be said about the phase of this signal with reference to the phase of the 5.25-MHz signal oscillating in the receive circuit is that it is indeterminate. The superposition of the 5.0-MHz signal and the already present 5.25-MHz oscillation in the receive circuit is modelled in FIG. 6B. The superposition of the two signals generates either a diminishment or enhancement of the envelope of the sum of the two signals depending on how out-of-phase or in-phase the two signals are. FIG. 6B is intended to depict how the superposition of the two signals, when the 5.0-MHz control signals are applied to the tristate switch, can be thought of as the simple addition of two oscillators. This analogy holds true only for a short time after the transmit circuit is re-activated and is presented to provide a better understanding of the interaction between the two signals.

FIGS. 7A and 7B show the signal generated by the steady-state model of FIG. 6B. It should be noted that the 5.25-MHz+5.00-MHz signal has the smallest amplitude when the phase difference between the two contributing signals is 180° (completely out of phase). As has already been noted, the behaviour of the link shown in FIG. 6A is approximated by the circuit of FIG. 6B for a short time after the 5.0-MHz signal is switched onto the already present 5.25-MHz oscillation in the receiver. By switching on the 5.0-MHz signal at a pre-calculated time, it is possible to ensure that it is summed with the 5.25-MHz signal when the phase difference between the two is approaching 180° and so induces a minimum at the output of the receive circuit.

In the case where the amplitude of one of the oscillators is less than the other (e.g., in FIG. 7B the output of OSC 2 of FIG. 6B has been attenuated to one-third that of OSC 1) a waveform will result with greatest diminishment of the envelope where the two waves are 180° out of phase, but not as pronounced as in the case where the two oscillator signals are of equal amplitude.

If the number of cycles below and above a fixed threshold are counted, then these numbers would differ as the amplitudes of the two generator signals are varied. An analogous effect occurs in the inductive link. Depending on the distance between the two coils, the amount of energy coupled into the receive coil will change and the amplitude of the induced 5.25-MHz signal will also change; consequently, the depth of any nulling achieved will be variable depending on the inter-coil coupling, which is in turn dependent on the inter-coil distance.

Figure 8:
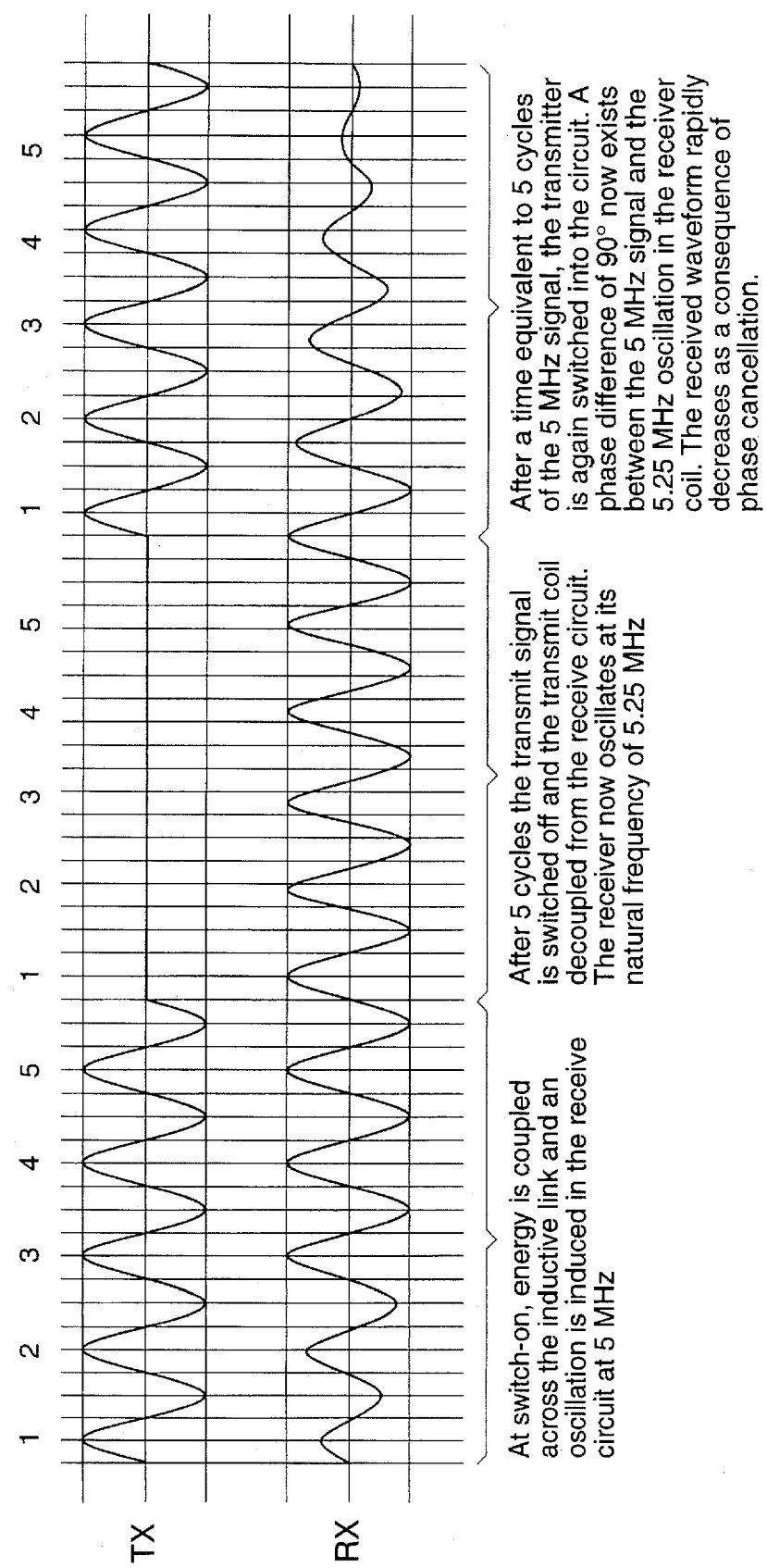
FIG. 8 illustrates the ideal response of the receiver to a transmitted signal when a 0 cell is transmitted between two 1 cells.

The effect of the summation of two out-of-phase signals in the actual circuit is shown in FIG. 8. The offset tuning of the transmit and receive coils, and the ability to couple and decouple the coils by means of the tristate switch, make it possible to produce phase cancellation and nulling at the output of the receiver. The upper waveform of FIG. 8 depicts the transmit circuit operating for five cycles, then turning off for five cycles, and then turning on once again for five cycles. It is assumed that initially there is no current flowing in the receive coil. The receiver takes a short time to build up to a steady-state level. As shown on the left side of the bottom waveform, at switch-on of the transmit circuit, energy is coupled across the inductive link and an oscillation is induced in the receive circuit at 5.0 MHz. After five cycles, the transmit signal is switched off and the coils are decoupled. The receiver therefore oscillates at its natural frequency of 5.25 MHz, with a slight decay (not shown) depending on the Q of the circuit.

After five cycles, the transmit circuit is turned on once again and driven at 5 MHz. It should be noted that the signal in the receive coil is now at a maximum when the transmission begins. This means that the 5.25-MHz signal in the receive coil is 90° ahead of the 5.0-MHz signal which is induced in the coil. This is equivalent to 50 nanoseconds. The sum of the two signals rapidly decreases when they start 90° out of phase. By monitoring the output at the receive side, it is possible to detect that the transmitter has been turned on and off, as the induced null will be apparent.

Perhaps the most significant feature of the waveforms of FIG. 8 is that the decrease in the amplitude of the signal in the receive coil, which decrease is indicative of five missing cycles in the transmit signal, is not actually detected until well into the operation of the transmit circuit once again. It is the starting up of the transmit circuit that forces the receive circuit to rapidly exhibit a decrease in its output so the fact of the earlier cessation of transmission can actually be detected.

Figures 9C, 12:
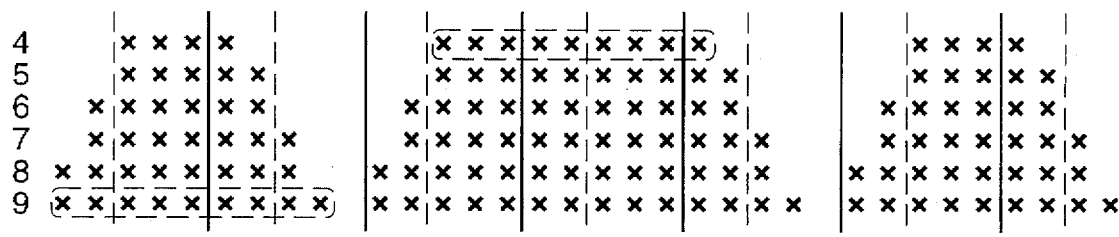
FIG. 9C illustrates a potential ambiguity.
FIG. 12 is a table which depicts the subsets of 6-cell tokens used in the illustrative embodiment of the invention.

One of the complicating factors in the transmission scheme of the invention is that the coupling coefficient between the transmit and receive circuits can vary appreciably, giving rise to a hulling effect which can be very substantial as shown in FIG. 7A, or less pronounced as shown in FIG. 7B. The encoding and decoding schemes must take into account the fact that the inter-coil coupling can be varied. How the coupling imposes certain conditions on the decoding is depicted in FIGS. 9A–9C.

In the illustrative embodiment of the invention a 1 bit is encoded as five cycles of the transmit signal (FIG. 5C operation for 5 cycles), and a 0 bit is represented by turning off the transmit signal for the same period of time (FIG. 5D operation for 5 cycles). This is only one example, and 0 and 1 bits may be represented by other, even different, numbers of cycles. It is also possible, of course, to use other frequencies for the tuning and driving of the transmit and receive circuits, although in the illustrative embodiment of the invention the operation is centered on the use of a 5.0-MHz driving frequency. The intent of FIG. 9B is to show that depending on the coupling between the transmit and receive coils, the waveform in the receive circuit will vary so that the number of cycles detected above a detection level threshold will not be constant for each transmitted 1 bit.

The waveform in FIG. 9A represents the current in the transmit coil for the transmission of six successive bits 101101. Each 1 bit is represented by five RF cycles, and each 0 is represented by the suppression of five RF cycles. FIG. 9B shows the signal in the receive coil induced by transmission of the waveform in FIG. 9A for two inter-coil separations. The upper waveform is the receive signal with the coil separation distance being such that the extent of nulling induced by the interaction of the 5.0-MHz cycles with the oscillating signal in the receiver coil is quite pronounced in comparison with the lower waveform where the nulling is shallower and many more cycles exceed detection level threshold. The detection level threshold (whose value will be defined) is superimposed on both waveforms; the X's in FIG. 9B mark RF cycles which exceed the detection level, i.e., which have been detected.

The upper waveform in FIG. 9B shows 5 RF cycles exceeding the threshold level for each 1 bit that is transmitted. The lower waveform of FIG. 9B shows nine RF cycles exceeding the threshold level for each 1 bit that is followed by a 0 bit. For two 1 bits followed by a 0 bit, there are an additional 5 X's, or a total of 14. It is significant that for each transmission of a 0 bit, there must be at least one cycle in the receive circuit that falls below the threshold level or else the 0 bit cannot be detected. It is assumed that there is at most one 0 bit between two successive 1 bits, although multiple 1s can be transmitted in sequence. Consequently, the only way that a 0 can be detected is if there is at least one cycle missing in the receive circuit, i.e., one cycle below the threshold level. The lower waveform in FIG. 9B shows a case exhibiting low inter-coil coupling. In this case, a 1 bit causes the receive circuit to oscillate so that the five RF cycles in the transmission are exhibited in the receive circuit output, as well as an additional four cycles which are due to ringing and which are not nulled below threshold because of the low inter-coil coupling.

FIG. 9C shows the total number of cycles detected in the receive circuit for a range of conditions, including that of the upper waveform of FIG. 9B (the row labelled 5 in FIG. 9C) and that for the lower waveform of FIG. 9B (the row labelled 9 in FIG. 9C). For different degrees of coupling, 4,5,6,7,8 or 9 cycles are detected in the receive circuit for any 1 bit that is transmitted, with an additional 5 cycles being detected for additional 1s that follow. In the most highly (tightly) coupled case illustrated, it is possible for only 4 cycles in the receive circuit to exceed the threshold level for each 5 cycles transmitted (although, once again, for each 1 bit which follows a preceding 1 bit, there are an additional 5 cycles above threshold). Thus the first row in FIG. 9C illustrates the case of 4 cycles being detected in the receive circuit when an isolated 1 bit is transmitted.

As the coils are moved closer and further away from each other, the number of receive carrier cycles that are above the threshold will change. FIG. 9C shows that an ambiguity will arise if all sequences of 4–9 carrier cycles above the threshold are interpreted as the reception of a bit of value 1. This is shown by the two groups (or "bursts") of circled Xs in FIG. 9C. For a tightly coupled condition, row 4 of FIG. 9C, there are 9 cycles which exceed the threshold level when two 1s are transmitted in sequence. Yet for the most loosely coupled condition there are 9 such cycles detected when only a single 1 is transmitted.

The general conditions under which such an ambiguity will arise can be determined as follows. Let N be the number of cycles transmitted signifying a 1 bit, and let P be the number of successive 1 bits transmitted. Of these P bits, P−1 of them give rise to N cycles each in the receive coil. The Pth bit (which of the P bits it is not important, as long as P−1 of the bits produce N(P−1) cycles in the coil; if N(P−1) cycles are not produced, the link is not usable) gives rise to a variable number of cycles R depending on coil coupling, circuit designs, and other variables. If a total of K cycles are detected, then K=R+N(P−1).

Let $[R_{low}, R_{high}]$ be the range of R=K−N(P−1), where K is the number of successive cycles detected in the receive coil with P and N constant and inter-coil coupling varied over its total expected range of in-field use. R will vary due to variations in link behaviour determined by such parameters as inter-coil coupling, inter-coil distance, and variation in Q of transmit and receive resonant circuits. For the link to be operative, R must be at least 1.

In order to unambiguously decode the incoming data stream, the case where P "1"s are transmitted (generating $N(P-1)+R_2$ cycles detected above threshold) must not be confused with the case where P+1 consecutive "1"s are transmitted (generating $NP+R_1$ cycles detected above threshold, where $R_2 > R_1$).

Suppose that P+1 "1"s are transmitted at an inter-coil coupling giving $R_1$. If the inter-coil coupling begins to vary, then the value $R_2$ at which a decoding ambiguity will first appear will be when:

$$NP + R_1 = N(P - 1) + R_2$$

$$NP + R_1 - N(P - 1) = R_2$$

$$R_2 = R_1 + N$$

For example, if $R_1$=4, N=5 and P+1 bits of value 1 are transmitted, then the same number of cycles will be detected when P+1 bits are transmitted if the coil coupling changes to a degree characterised by $R_2$=9 in the receive circuit. That is, the only variations in coil interaction can be tolerated are those that result in R varying in the range of [$R_1$, $R_2$–1 if there is to be no decoding ambiguity.

In general, [$R_1$,$R_2$] will be a sub-range of [$R_{low}$,$R_{high}$] observed from experiment to occur most frequently. In order to correctly detect a 0 between two 1 bits, e.g., in the sequence 101, the largest value of $R_2$ can be no greater than N+M–1, where M is the number of missing cycles by which a 0 is represented. Often N=M, so that $R_2$ must be less than 2N. This is so that at least one of the cycles resulting from the sequence 101, and corresponding to the 0 bit, falls under the detection threshold. The sub-range that satisfies these conditions is denoted [R',R*].

Data transmitted across a link exhibiting inter-coil couplings that generate values in the range of [R',R*–1] can be detected unambiguously using a single counting scheme.

For an inter-coil coupling condition resulting in R*–1, the number of cycles detected will be N(P–1)+(R*–1). Similarly, for an inter-coil coupling condition resulting in R', the number of cycles detected will be N(P–1)+R' Therefore, it can be stated with certainty that P "1"s were transmitted when K cycles are detected in the range $$N(P-1)+R' \leq K \leq N(P-1)+(R*-1)=N(P-1)+R'+N-1=NP+R'-1. \quad (i)$$

For example, suppose N=5, P=1, and R'=4. Then (1) R*=4+5=9 (condition at which ambiguous decoding will first occur), and (2) If between 5(1–1)+4 and 5(1)+4–1, i.e., [4,8] cycles are detected, then it is known that P=1, i.e., a single bit comprised of 5 cycles was transmitted.

Suppose next that N=5, P=2, and R'=5. Then (1) R*=R'+N=10 (the coil interaction that generates this value of R causes the ambiguity to commence), and (2) If between 5(2–1)+5 and 5(2)+5–1, i.e., [10,14] cycles are detected, then it can be stated with certainty that P=2, i.e., two consecutive bits comprised of 5 cycles each were transmitted.

In general, if K cycles are detected with R' and N known, then it is possible to determine P, the number of 1 bits transmitted, as follows. From (i), N(P–1)+R'≤K≤NP+R'–1. Solving for P, $$(K+1-R')/N \leq P \leq (K-R')/N+1. \quad (ii)$$

The link is constrained so that the [R',R,–1] range is [4,4+N–1]. If, for example, 17 cycles are transmitted and N=5, then $$P \leq (17-4)/5+1=3.6 \text{ and } P \leq (17+1-4)/5=2.8.$$

Since P is an integer, it must be 3.

As a further example, let R'=4 and N=5. Then if between 15 and 20 cycles are counted (i.e., K is between 15 and 20), the number P will be as shown:

| K  | ≤P ≤ |     | (P) |
|----|------|-----|-----|
| 15 | 2.4  | 3.2 | 3   |
| 16 | 2.6  | 3.4 | 3   |
| 17 | 2.8  | 3.6 | 3   |
| 18 | 3.0  | 3.8 | 3   |
| 19 | 3.2  | 4.0 | 4   |
| 20 | 3.4  | 4.2 | 4   |

There will never have to be a choice made to determine the value of P because the range of P defined by inequality (ii) can be shown to be (N–1)/N which is less then 1 for all positive values of N.

This procedure defines a range over which inter-coil transmission properties may be allowed to vary without introducing ambiguity into the determination of P. This range is [R',R*–1]. Therefore, in order to unambiguously determine P, the user first ascertains the likely range over which R will vary, i.e., [$R_{low}$,$R_{high}$]. From this experiment the subrange [R',R*–1] that is most likely to be encountered in the field is selected. So long as the coil conditions are constrained to generate only R values that fall within [R', R*–1], it is possible to determine P unambiguously by using inequality (ii).

It has been found that transmission of an isolated 1 bit ,e.g., the 1 in 010, can give rise to a special decoding case in that when P=1 it is possible that less than K=R' cycles may be detected. In order that these bits are recognized, an isolated 1 bit is accepted as having been detected if less than R' cycles are counted. For example, if R'=4 it may be reasonable to assume that a 1 was transmitted if only 2 or 3 cycles are counted.

A particular feature of the link is that it is highly resistant to any introduction of errors due to parasitic capacitances that are unavoidable to some extent in any implementation. Experiments have shown that while the receive coil is tuned to 5.25 MHz, parasitic capacitances alter the actual resonant frequency by up to 6% and also prevent complete decoupling of the coils during the transmission of 0 bits. It has been found that the result of this is that, at the start of the transmission of a 1 cell, instead of there being a 90° phase difference between the current which is already oscillating in the receive coil and the received signal, as shown at the start of the third cell in FIG. 8, the difference is closer to 180°. The nulling which is forced by the transmitted signal thus occurs closer to the start of the cell, toward the beginning of the five cycles, rather than toward the end as shown in the non-parasitic affected case depicted in FIG. 8. The overall effect, however is as described above—in the case of loosely coupled coils, a missing RF cycle, representing a 0 cell, is detected while the next 1 cell is actually being received.

Figure 10A:
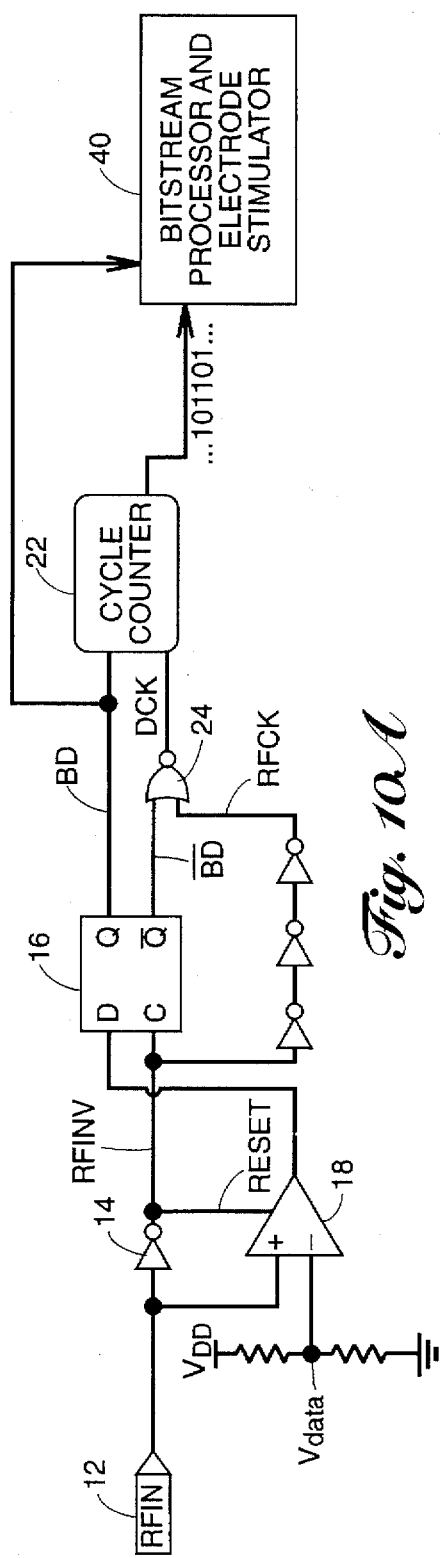
FIG. 10A is the schematic of the decoder utilized in the illustrative embodiment of the invention.

FIG. 10A is a circuit for detecting successive received bits capable of accommodating the variation in the number of received cycles detected as illustrated in FIGS. 9A–9C, and FIG. 10B depicts the signal in the receive circuit that the detector operates on as well as three intermediate digital waveforms that are required to reconstitute the bitstream originally transmitted by the data transmitter.

Figure 10B:
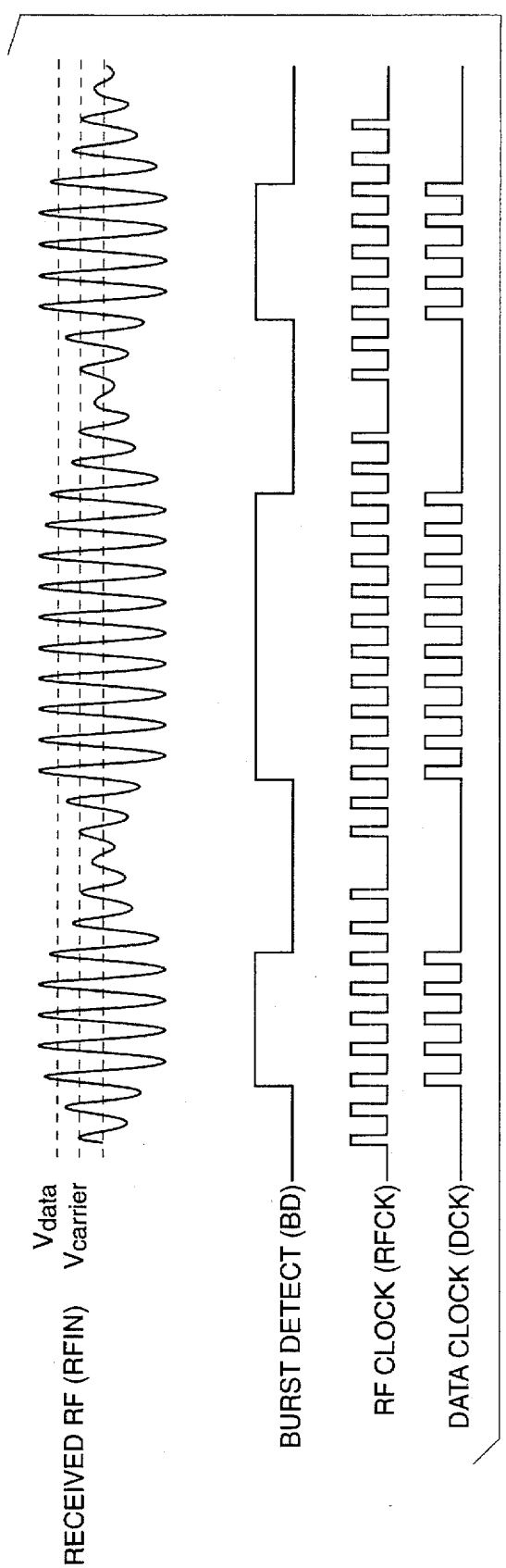
FIG. 10B illustrates certain waveforms characteristic of the operation thereof.

It is assumed that the signal at the RFIN (RF input) pin 12 is of the form shown in the uppermost waveform in FIG. 10B. The input signal is processed by inverter 14 and passed to the clock input of D-type flip-flop 16. The inverter has an in-built threshold $V_{carrier}$ whose relative level is shown in FIG. 10B. The RF input is also extended to the non-inverting input of comparator 18, whose output is connected to the D input of the flip-flop. The reference of the comparator, $V_{data}$, is derived from a voltage divider connected to potential source $V_{DD}$. The Q output of the flip-flop is labelled BD (burst detect), and is extended to the cycle counter 22. The output of inverter 14 is connected to the reset input of the comparator, and is also extended through three inverters, which introduce a delay, to an input of NOR gate 24, the other input of which is connected to the inverted Q output of the flip-flop. The DCK (data clock) output of the NOR gate is extended to the cycle counter which operates according to a scheme that will be explained below. Two outputs of the overall decoder are the bitstream output, taken from the cycle counter, and the BD (Burst Detect) output from the flip-flop. These outputs are passed on to the Bitstream Processor and Electrode Stimulator 40. The Bitstream Processor converts the bitstream from token form to standard binary form, as will be explained below, and incorporates an algorithmic state machine for retrieving the coded amplitude, electrode and mode data necessary to perform the appropriate biphasic stimulations. The duration of each phase of the stimulation is determined by monitoring the Burst Detect signal.

The lower three waveforms in FIG. 10B depict the BD (burst detector) output of the flip-flop, the RF clock, and the data clock output from the NOR gate.

The actual decoding process is depicted in FIGS. 11A–11D which show intermediate waveforms for some of the subsystems in the overall decoder. The following description should be applied against the drawings of all of FIGS. 10A, 10B and 11A–11D.

The circuit operates on the received RF (RFIN) to derive the Burst Detect (BD) and Data Clock (DCK) signals which are then used by cycle counter 22 to count the number of received cycles that are above the data threshold in order to retrieve the transmitted data stream.

The signal on RFIN pin 12 is split into two parts, one going to saturating inverter 14 and the other to the non-inverting input of comparator 18. The inverting input of the comparator is connected to a voltage divider reference $V_{data}$ derived from a potential $V_{DD}$. The $V_{DD}$ potential can be thought of as a peak detector operating on the $V_{out}$ potential of FIG. 3, including a supply capacitor that is charged by the rectified RF signal. The derivation of a power source from the transmitted RF signal is standard in the art. The voltage divider used to derive the $V_{data}$ potential thus varies as a function of the amplitude of the incoming RF and is a measure of the maximum amplitude.

Figure 11A:
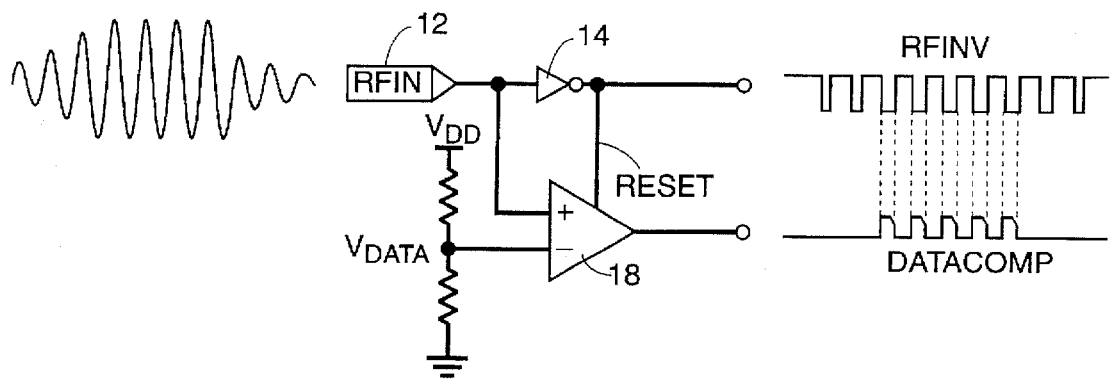
FIGS. 11A–11D illustrate in greater detail the operation of the decoder, in terms of both waveforms and individual sections.
Figure 11B:
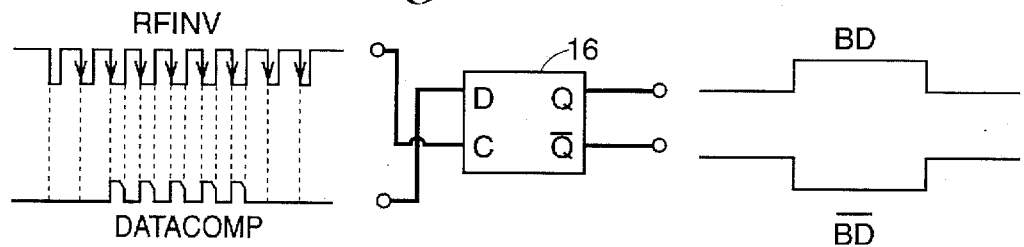

Referring to the top waveform of FIG. 10B, whenever a signal exceeds the $V_{data}$ level, it is considered to correspond to a cycle of transmitted RF. In the drawing of FIG. 11A, RF cycles above the $V_{data}$ threshold generate the pulses in the DATACOMP (data comparison) waveform. It should be noted that each DATACOMP pulse has a short rise time, a peak level, a slow decrease, and finally a sharp fall to a base level. The reason for the sharp rise is that the comparator reacts quickly when the RFIN signal exceeds the $V_{data}$ level. As the RFIN signal falls toward $V_{data}$, the DATACOMP output falls back toward the base level. This is represented by the slowly decreasing segment of each pulse. The particular comparator used has a slow fall time and without reset its output would ordinarily fall for a longer time than shown. However, each DATACOMP pulse is forced back to the base level quickly because the output of inverter 14 applies a positive potential to the reset input of the comparator when the RFIN signal falls below $V_{carrier}$.

Inverter 14 operates on the RFIN input. The inverter has a threshold which is set to about 40% of the maximum amplitude of the received RF signal. This level is labelled $V_{carrier}$ and is shown in the upper waveform of FIG. 10B. (The $V_{carrier}$ level can be derived from a peak detector, not shown, as is known in the art. Alternatively, inverter 14 can be thought of as including a peak detector for deriving the threshold level.) The inverter in fact operates as a comparator with an in-built threshold and inverted output. When the output of the inverter, RFINV (RF inverted), goes high, it resets comparator 18 and the DATACOMP output goes low.

The net result is that when the RFIN input exceeds the $V_{data}$ level, a pulse appears in the DATACOMP output of comparator 18. When the RFIN input falls below the $V_{carrier}$ level, the DATACOMP pulse terminates. This is shown most clearly in FIG. 11B. Each rising edge (non-arrowed edge) of the RFINV signal resets the comparator and so forces the DATACOMP output low.

The RFINV and DATACOMP signals are fed respectively to the C and D inputs of D-type flip-flop 16. The flip-flop is clocked by a falling edge in the RFINV waveform, shown by arrows on the RFINV waveform in FIG. 11B. If the D input is high at clocking time, representing the presence of a DATACOMP pulse, the Q output of the flip-flop goes high and the inverted Q output goes low. As long as there is a DATACOMP pulse, high on each falling edge of the RFINV clock, the flip-flop remains set. The reason for providing a short rise-time in the comparator is to ensure that the DATACOMP pulses will be high and stable when the clocking edges of the RFINV waveform occur. The flip-flop changes state, not on the trailing edge of the last DATACOMP pulse in a series, but rather when the RFINV clock next goes low after the last pulse in a group of DATACOMP pulses has terminated. This is shown most clearly in the inverted BD signal at the input of the circuit of FIG. 11C which is shown relative to the RFINV and DATACOMP waveforms. The reason for providing a reset input to the comparator is to ensure that the output of the comparator goes low before the next clocking of the flip-flop, i.e., to ensure that the D input of the flip-flop is stable at the clock edge.

The BD pulse stands for a "burst detect" and a single BD pulse represents the transmission of a series of RF pulses, representing one or more successive bits of value 1 (or, as discussed above, "cells" of value 1). Referring to FIG. 9C, depending on which scheme is implemented for the transmission of a single 1 between two 0s, there may be anywhere between 4 and 8 DATACOMP pulses, or anywhere between 5 and 9 in a group corresponding to the transmission of a 1. The drawing of FIG. 11B happens to be for the coupling condition where 5 pulses are generated. For each additional 1 bit (cell) which is transmitted in the same sequence, there will be another 5 DATACOMP pulses within the same BD pulse. Thus a single BD pulse is high while the RFIN waveform is deemed to contain information concerning the transmission of logical 1s. The exact number of logical 1s depends on how many RFINV pulses occur during the time the BD waveform is high and is determined unambiguously by the cycle counter as will be explained below.

It is critical that the flip-flop be reset at the end of a DATACOMP pulse sequence in order that a 0 in the transmission be detected. Such an event triggers the end of the BD pulse. This requires that there be an RFINV clock after the last DATACOMP pulse in series. This, in turn, means that the inverter 14 must be able to operate on another RF input pulse after the last RF input pulse in a series that is detected by the comparator 18. Referring to the upper waveform in FIG. 10B, this necessitates that the first RF cycle in a sequence that falls below the $V_{data}$ level, and so heralds the transmission of a 0 cell, must nevertheless exceed the $V_{carrier}$ level. This is the only way in which the flip-flop can be clocked after a group of DATACOMP pulses so that the BD pulse goes low to indicate that a 0 has been received. In the illustrative embodiment of the invention, for coils separated by approximately 2–10 mm and with each cell including 5 RF clock cycles, it has been found that $V_{data}$ and $V_{carrier}$ levels that are 80% and 40% of the peak level of the received RF insure that the Q output of flip-flop 16 always goes low at the end of the transmission of a series of 1 cells. Of course, this assumes that the transmitter and receiver circuits are offset tuned as discussed above so that a 0 cell which would not otherwise be detected is in fact detected when the next 1 cell forces the amplitude of the signal in the receive coil to drop below the $V_{data}$ level.

Figure 11C:
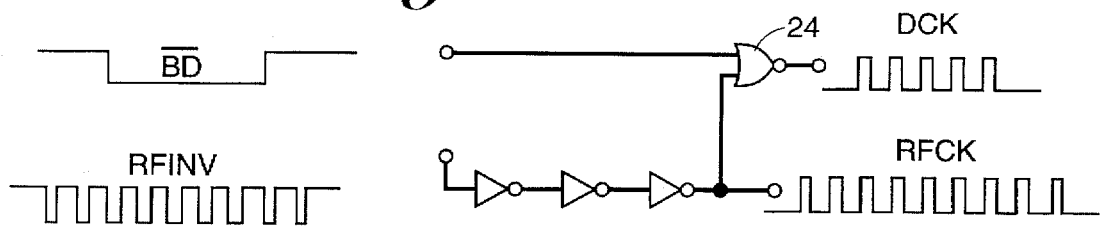

As shown in FIGS. 10A and 11C, the RFINV signal is extended through three inverters to generate the RFCK waveform. The three inverters simply introduce a short delay, as well as invert the overall RFINV signal. The RFCK signal serves as the basic system clock. It is delayed slightly relative to the BD and inverted BD signals to allow the latter to settle before being operated on by NOR gate 24.

Figure 11D:
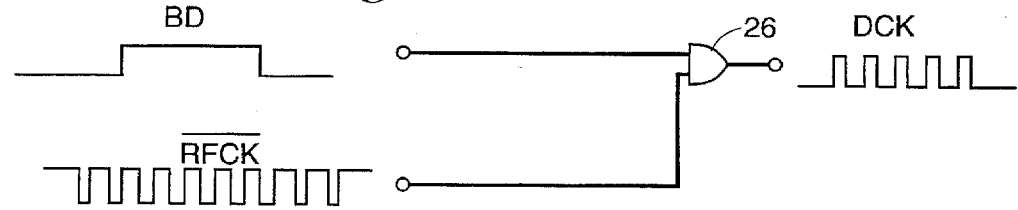

FIG. 11D depicts an AND gate 26. By De Morgan's theorem, an AND gate with two inverted inputs is equivalent to a NOR gate with non-inverting inputs. Thus instead of considering NOR gate 24 having RFCK and inverted BD inputs, we can consider AND gate 26 having inverted RFCK and BD inputs. From FIG. 11D it can be seen that DCK is simply the ANDing together of BD and the inverted RFCK stream which consists of a series of rectangular waves, i.e., the envelope of the rectangular wavestream is determined by BD.

Consequently, DCK consists of groups of rectangular pulses with each group containing the same number of pulses as there were received carrier cycles above threshold in the received group of carrier cycles comprising the original RFIN signal. It is the DCK pulses that are actually counted in cycle counter 22 of FIG. 10A to determine how many successive 1 cells have been transmitted.

The cycle counter reconstitutes the originally transmitted bitstream by monitoring the BD and DCK waveforms. The cycle counter implements a system for determining P by solving the inequality $(K+1-R')/N \leq P$, i.e., $(K-(R'-1))/N \leq P$, which was previously derived. The scheme is as follows:

I) Discard the first $R'-1$ cycles in the burst and reset the modulo N counter, i.e., introduce a counting offset so that counting begins on the R'th detected cycle.

II) Count all remaining cycles in the burst, generating a flagging event on every count of 1 of the modulo N counter.

III) The number of flagging events generated during the burst is equal to P.

Figure 17A:
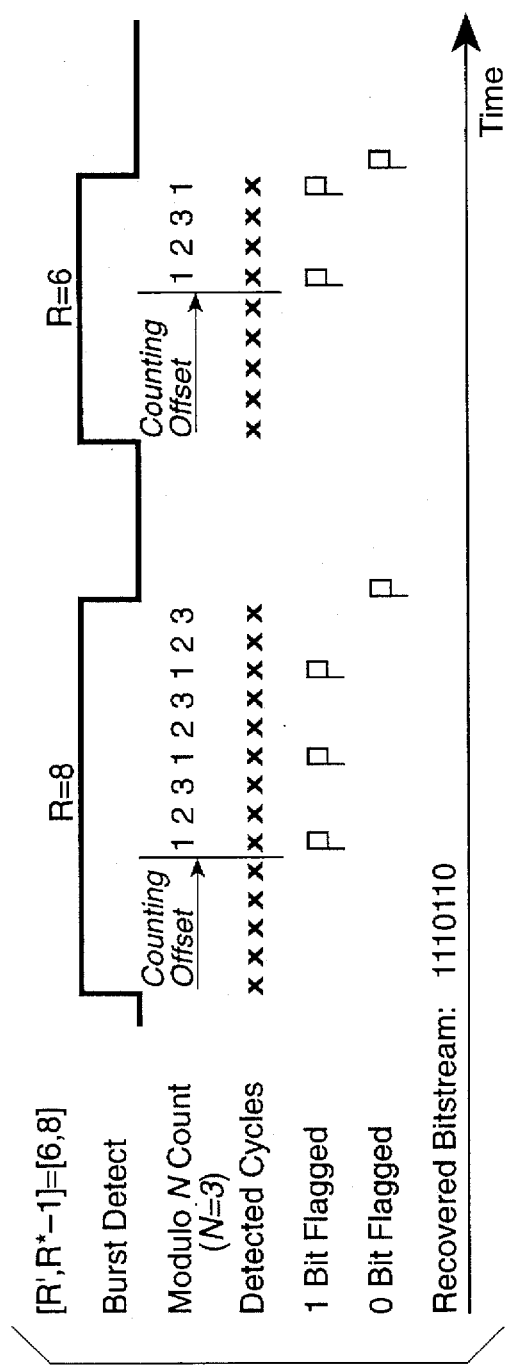
FIGS. 17A and 17B illustrate the operation of the cycle counter while the degree of inter-coil interaction is varied for cells of 3 and 5 cycles.
Figure 17B:
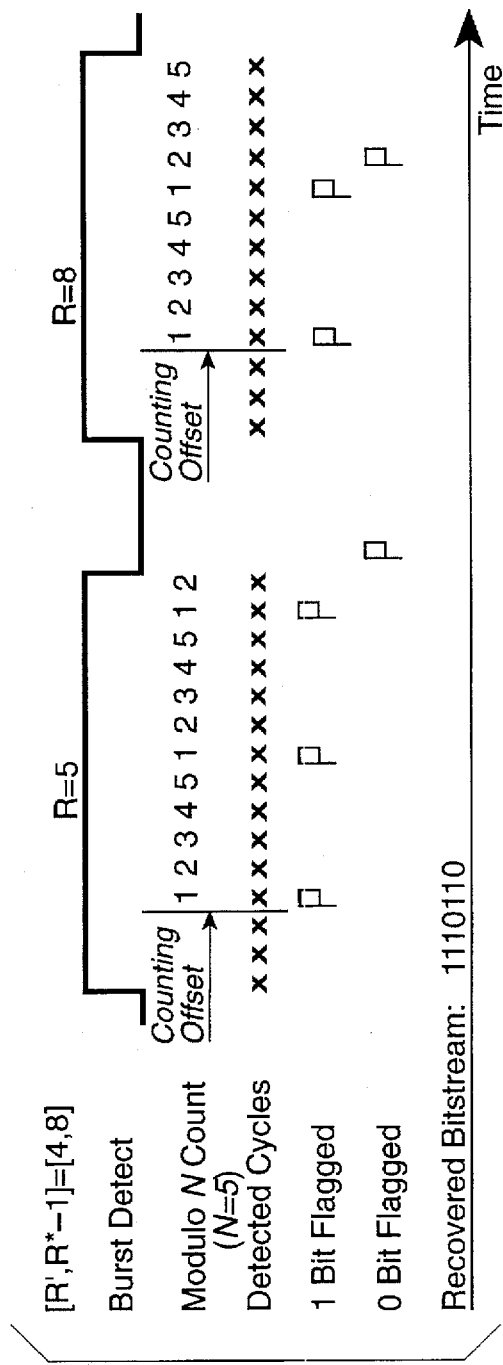

The cycle counter is reset and flags a single 0 whenever BD goes low. It commences counting again when more DCK pulses are incoming. Note that this means that the receiver decoder does not check the duration of a 0. A 0 is always assumed by the decoder as having a single occurrence. FIGS. 17A and 17B illustrate the decoding procedure. In FIG. 17A the inter-coil interaction range is such that R varies over $[R', R^*-1]=[6,8]$, N=3, and P is determined over two bursts, being 3 in the first and 2 in the second. The variation of R is such that R=8 during the first burst and R=6 during the second. The counting offset is $R'-1=6-1=5$ so that 5 detected cycles are ignored before modulo 3 counting commences. Similarly, FIG. 17B depicts the decoding situation where the inter-coil interaction range is such that R varies over [4,8], N=5, and P is determined to be 3 in the first burst and 2 in the second. The variation of R is such that R=5 during the first burst and R=8 during the second. The counting offset is $R'-1=4-1=4$ so that 3 detected cycles are ignored before modulo 5 counting commences.

One way to implement the cycle counter is to utilize a microprocessor with appropriate software, using the rules just set forth. Alternatively, a custom state machine decoder may be implemented in a low power, e.g., CMOS logic circuit. As shown in FIG. 10A, the output of the cycle counter is a bit stream. The remaining circuitry of the cochlear prosthesis, such as that shown in the Crosby et al. patent discussed above, then operates on this bit stream in order to derive the stimulating signals for the electrodes. However, as part of this processing (which can be implemented in cycle counter 22 or separately) it is necessary to convert the bit stream shown in FIG. 10A to another bit stream for reasons discussed above but now to be described in greater detail.

As just described, the cycle counter outputs a single 0 when the BD pulse goes low. This is an indication that a burst of RF cycles has stopped, and that a preceding sequence of 1 cells has terminated. The cycle counter determines that only a single 0 has been received no matter how many RF cycles are now missing. Thus it is important that no attempt be made to transmit two or more consecutive 0s, as they would be detected as only a single 0. Since a straight binary coding scheme allows successive 0s, it is apparent that a straight binary coding scheme cannot be employed. By disallowing two or more successive 0s, the detection scheme can be made very reliable and continuous in operation without any gaps within each data block, as will be discussed below. Furthermore, by transmitting many more 1s than 0s, and using RF cycles to represent 1s and the absence of RF cycles to represent 0s, the duty cycle can be made as high as 75%, one of the objectives of the invention.

As discussed above, the receiver/stimulator (RS) energizes the electrodes in the electrode array depending on instructions received in the serial data stream transmitted from the wearable speech processor (WSP). Clearly, the data rate will be higher if the data can be transmitted continuously and analyzed by the RS while electrode stimulation is taking place, rather than delaying stimulation of the electrode array until after data for that stimulation is transmitted. The embedded protocol of the invention allows for the simultaneous transmission of data while electrode stimulation duration is being controlled by the information signal being transmitted.

To stimulate the RS using the scheme of the above-identified Crosby et al. patent, it is necessary to encode 18 bits of data, 5 bits for the E data, 5 bits for the M data and 8 bits for the A data, together with duration information for the Phase 1 and Phase 2 pulses in each biphasic pair. It is desired that a stimulation rate of up to almost 20,000 pulses/second be achieved. There is additional overhead required due to the need for data synchronization and error detection. The minimum RF frequency is determined by the fact that a 1 is said to have been transmitted when the 5-MHz control signals have been applied to the tristate switch of FIG. 3 for five complete cycles, and a 0 is said to have been transmitted when the control voltages applied to the tristate switch have caused decoupling of the tuned circuits for five complete cycles. There are two additional constraints which limit the choice of encoding scheme. The first is that the RF duty cycle should be as high as possible, preferably about 75% during data transmission in order to supply the RS with sufficient power for its correct operation. The second constraint is that a 0 always be preceded by a 1 since a 0 is the cessation of RF transmission and this means that a 1 must be transmitted before a 0 can start.

As discussed above, a cell or bit, as it is transmitted, consists of 5 RF cycles, or the absence of cycles for a period corresponding to 5 RF cycles, representing respectively 1 and 0. As used herein, a "token" is a series of six such bits, thus requiring a transmission time equivalent to 30 times the period of the RF carrier. Since a 0 cannot even be detected unless it follows a 1, because a 0 is detected by the cessation of the transmission of RF cycles and this necessarily requires that RF cycles be transmitted in the first place, of the 64 tokens that are possible with 6-bit combinations, only the half of them that begin with a 1 can be valid. Tokens should begin with a 1 because there is no feasible way to detect a 0 if it is the first bit transmitted. Of the 32 possible 6-cell tokens with a leading 1, the tokens that are selected for transmission are taken from those that have non-consecutive 0s, and either only one or only two 0s. The non-consecutive 0s criterion is required because, as discussed above, it is not possible to detect consecutive 0s. Selecting tokens that have the fewest number of 0s, only one or two, ensures that the duty cycle is as high as possible because bits of value 1 predominate. The only exception is the token 101010. This token is selected for use at the start of a frame, as will become apparent, because the alternating sequence of bit values cannot occur anywhere else during a data block, i.e., no six-cell "snapshot" during the transmission will be 101010 except this token. By using it at the start of each frame, the probability of not missing a frame, by reason of incorrectly detecting the first synchronization token, is minimized and the decoder is able to synchronize rapidly after power-up (the decoder powers up in asynchronous mode, searching the incoming data stream for 101010). It should be noted that at the highest frame rate, together with minimum (1 cell) phase extender (to be explained below), the transmitted RF will appear as a continuous data stream with no means for frame synchronization other than the synchronization tokens, i.e., the system does not rely on detection of frame gaps or long phase gaps for its data synchronization. The table of FIG. 12 depicts the 12 tokens which satisfy the specified criteria, including token 101010, and the data bits that they represent. It should be noted that 101010 is not the only possible synchronization token but has been chosen for this particular embodiment as the preferred Sync 1. It should also be noted that six-cell tokens have been used to represent tri-bits in the embodiment described. However, tokens comprised of other numbers of cells used to represent other than tri-bits are possible.

It must be understood that a 6-bit token does not represent 1 out of 64 possible separate pieces of data. In fact, because there are only 12 tokens, each token represents 1 out of 12 possibilities, and even these are not all data. Each token that signifies data represents three bits, and thus each token that conveys data really represents 1 of 8 possibilities. Referring to the table of FIG. 12, token Nos. 3, 4, 5, 7, 8, 10, 11 and 12 represent the 8 possible permutations of 3 bits. The first and second tokens are used for synchronization purposes. Two of the 12 tokens are not used at all.

Token No. 3 is used to represent the 3-bit sequence 011. This also happens to be the even parity error token as will be described, but at this point it is sufficient to treat this token as any other. Similar remarks apply to token No. 11 which, in addition to representing the bit sequence 111, is the odd parity error token.

Only ten tokens are required, eight which represent 3-bit data sequences and two which are synchronization tokens that precede respective halves of a frame. Since there are 12 tokens in all, two of them can be discarded. Token No. 9 is discarded because if this token, 111010, is followed by any other which begins with 10, a synchronization token might be detected erroneously since embedded in the overall bit sequence would be the Sync Ph1 token. When the decoder first powers up, it operates in a "free-running" mode in which it continuously scans the incoming data stream looking within a sliding 6-cell window for a Sync Ph1 token. Once it detects a Sync Ph1 token, it switches to synchronous decoding with a 6-cell token window referenced to the Sync token. If the Sync Ph1 detection was erroneous, the subsequent data stream soon becomes invalid due to formatting problems. In such a situation the decoder reverts to free-running mode until it locks onto a valid synch token. Thus, the exclusion of tokens 6 and 9 reduces the likelihood of the decoder making "false starts" and so delaying standard operation.

An inspection of the 10 tokens that are used reveals that 77% of the total number of bits are 1s, thereby achieving the necessary duty cycle criterion.

Figure 13A:
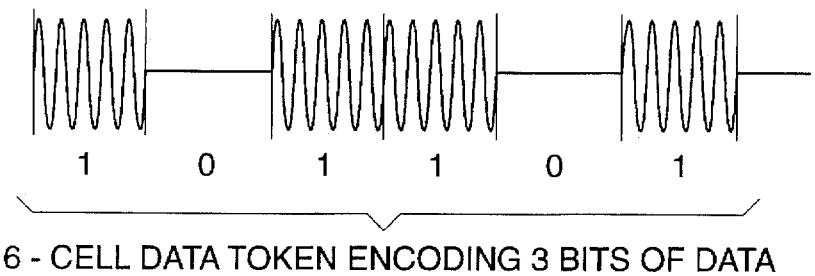
FIGS. 13A–13C depict the relationships between cells, tokens and data blocks.
Figure 13B:
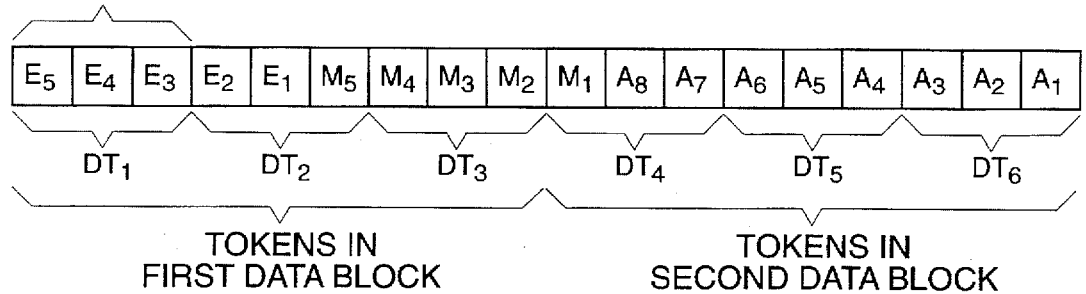
Figure 13C:
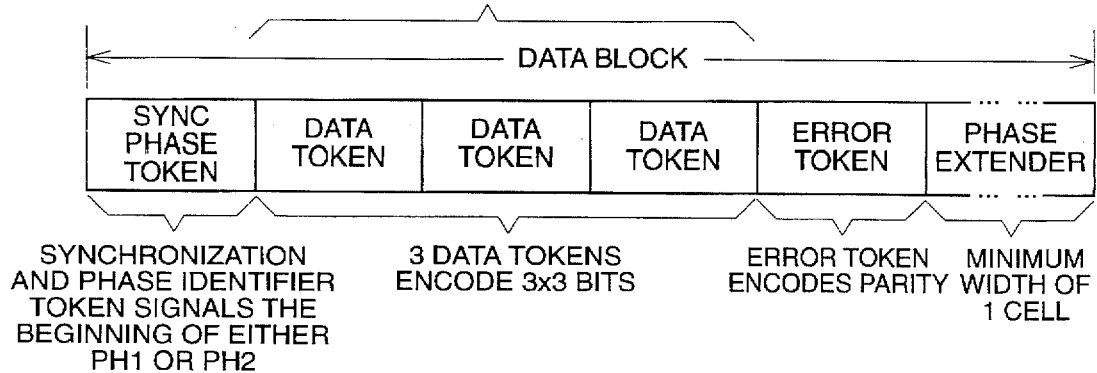

FIGS. 13A–13C show the coding scheme. FIG. 13A represents the 6-cell token 101101, with 5 RF cycles per cell. As shown in the table of FIG. 12, this token encodes the 3-bit sequence 011 and is also used as the even parity error token.

FIG. 13B shows how 6 tokens are required in each overall frame to represent 18 bits of data (3 bits/token). There are five E bits transmitted in the sequence $E_5$–$E_1$, five M bits transmitted in the sequence $M_5$–$M_1$, and eight bits transmitted in the sequence $A_8$–$A_1$. These 18 bits have to be allocated to 6 tokens, each of which represents 3 bits. The 6 tokens $DT_1$–$DT_6$ have the 18 bits allocated to them as shown in FIG. 13B. While FIG. 13B shows the 6 data tokens required in each frame, the data tokens are not transmitted one after the other. The first 3 data tokens are transmitted in the first data block of a frame, and the next 3 data tokens are transmitted in the second data block, as will become apparent.

FIG. 13C depicts the way in which all of the tokens are transmitted in each frame. There are two data blocks per frame, and FIG. 13C shows one of them. The first token which is transmitted is a sync phase token, either Sync Ph1 or Sync Ph2, depending on whether the data block is the first or the second of a frame. The sync phase token is followed by 3 data tokens which encode 9 of the 18 bits required for the frame. There follows an error token which encodes parity and allows for a check against code slip error, the failure to detect a 1 cell.

After the error token comes the phase extender part of the data block. The phase extender is of variable length and determines when the phase ends. The phase begins at the end of the sync phase token as will be described shortly. The respective half of the biphasic pulse begins with the first data token in the data block and ends at the end of the phase extender. The phase extender includes at least one 1 cell (5 RF cycles) but can otherwise be of any duration. The important point to note, of course, is that the actual pulse applied to the selected electrodes begins at the start of the first data token in the block. The way in which it is known which electrodes to stimulate is that the set-up data is transmitted in the preceding frame. It should be appreciated that if the design requires that for the implant to have sufficient power the duty cycle need not extend beyond 75%, then every fourth RF pulse can be omitted during the phase extender (determining the duration of one phase of the biphasic stimulation pulse). This has the effect of reducing transmitter power consumption which is of critical concern in a battery powered device. Due to the ringing that takes place in the receive coil, the system cannot detect a single missing pulse—no peak in the receive circuit actually falls below the $V_{data}$ level if only a single carrier cycle is missing between two other cycles.

Figure 14A:
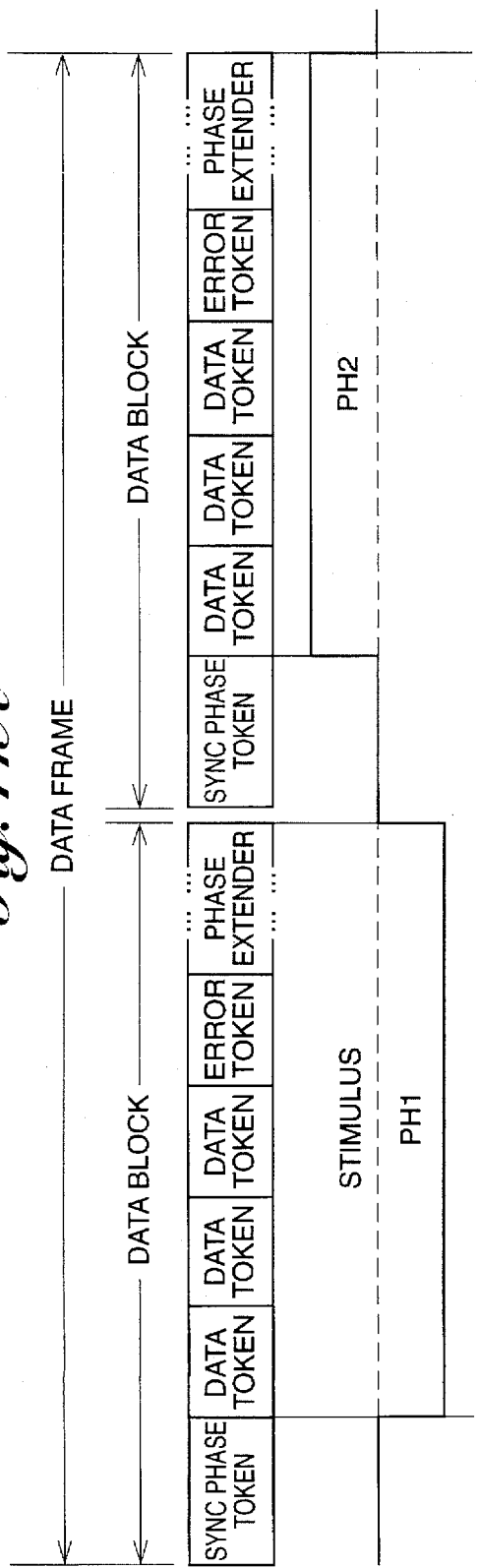
FIGS. 14A and 14B illustrate the relationship between data blocks and frames.
Figure 14B:
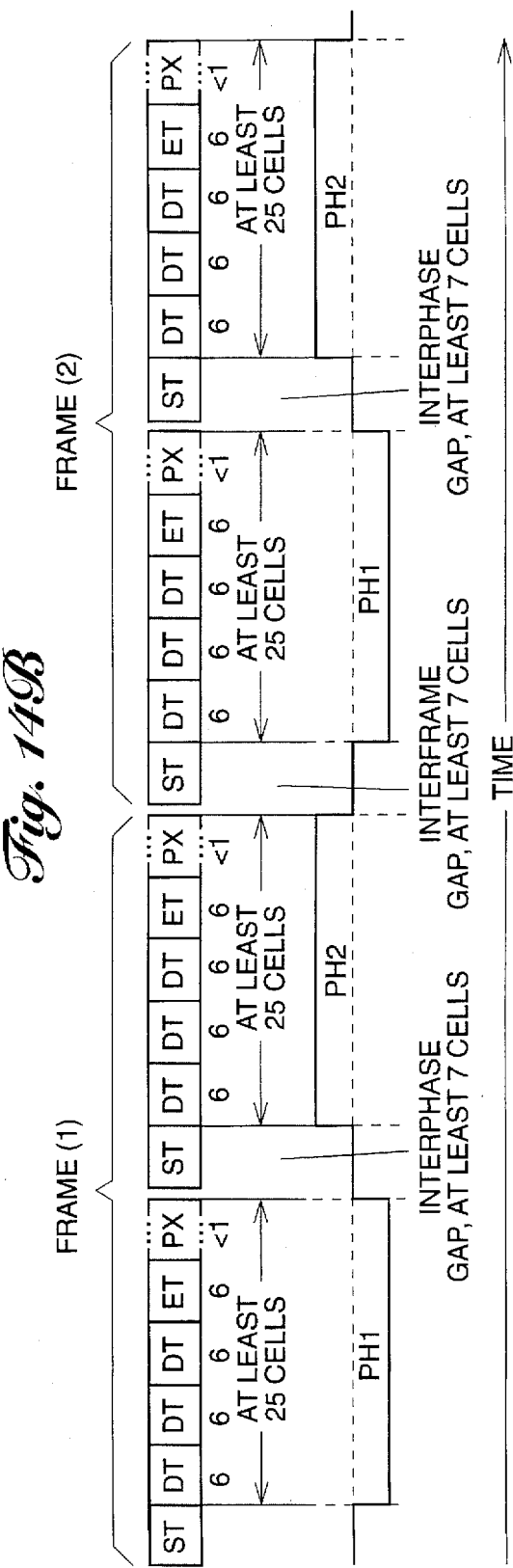

FIGS. 14A and 14B show the way in which an individual data frame and successive data frames are organized. As shown in FIG. 14A, a data frame consists of two data blocks, each as just described in connection with FIG. 13C. The two data blocks together contain 18 bits that determine all parameters, except duration, of the stimulation that takes place when the next frame is received, and 6 parity bits. For any frame, the first stimulus, Ph1, begins at the end of the Sync Ph1 token and ends at the end of the phase extender. The second half of the stimulus, Ph2, as shown in the drawing, starts at the end of the second sync phase token in the frame, Sync Ph2, and terminates at the end of the second phase extender.

The purpose of FIG. 14B is to show the way in which data embedded in one frame encodes the parameters required to generate the stimulus for the next frame. It should be noted that each stimulus phase is shown to have a duration of at least 25 cells. That is because the phase embraces 4 tokens with 6 cells in each, plus at least 1 cell in the phase extender part of the block. The requirement for at least one cell for the phase extender portion of each data block is to allow simplified system design. (It is easier to construct a system, in either hardware or software, if the same state sequencing takes place during each data cycle.) Thus by requiring every data block to end with at least 1 cell in the phase extender section, every data block can be processed in the same way. Although most phases will require multiple cells in the phase extender part of a data block, there are some which will not but which nevertheless have the extra cell. This results in a minimum phase extender duration of 1 μS for 5-cycle cells at 5 MHz. There is an interphase gap of at least 7 cells in the middle of each frame, as well as a minimum interframe gap of 7 cells. In other words, successive data blocks are separated by at least 7×5 or 35 RF cycle times—5 cycle times during which there is no transmission (which mark the end of the phase extender), and 30 during which a sync token is transmitted.

It must be understood what is meant by interphase and interframe gaps. The highest stimulation rate is achieved if there are no gaps between data blocks. However, every data block is preceded by a one-cell gap and then a sync token whose duration is 6 cells. Thus at least 7 cells (more if there is little stimulation required and the gaps can be made longer) are present in each data block without being useful in that no stimulation takes place during that time. These gaps do not affect power transfer because little power is required when a stimulation is not being applied.

With long phase extenders, the usual case, the duty ratio during a data block can exceed 75%, in which case every fourth RF pulse in a phase extender can be omitted altogether to lower the duty cycle back to 75% and thus conserve energy.

The table of FIG. 15 illustrates how the system of the invention permits very high stimulation rates. As just described, the first phase of a frame consists of a minimum of 25 cells, 6 cells for each of the data and error tokens, and at least 1 cell for the phase extender. At 5 MHz, the period of a cycle is 0.2 μsec. Therefore, with 5 cycles per cell, each phase lasts (5)(25)(0.2 μsec), or 25 μsec. The minimum interphase gap is 7 cells, and this takes 7 μsec. The same is true of the interframe gap. Therefore, the minimum time taken for a complete stimulation is (25+7+25+7) μsec, or 64 μsec. The maximum biphasic stimulation frequency is the reciprocal of this time, or 15.63 kHz.

If different numbers of cycles are used to represent cells, but the RF transmission is still at 5 MHz, then the maximum stimulation rate will vary. The table of FIG. 15 shows the applicable results where there are 4, 5 and 6 cycles per cell. With a higher transmission frequency, of course, the maximum stimulation rate increases proportionally.

The table of FIG. 16A and the matrix of FIG. 16B show how the 8 data tokens, together with the 2 parity tokens (which are two of the data tokens themselves) can be used to detect all single errors. If an error in a single cell (an error in a single transmitted bit of a token, before the tokens are translated into 3-bit sequences) gives rise to a token which is not one of the 8 permitted, then the system knows that an error has taken place and no electrodes are stimulated until synchronization is regained and error-free transmission takes place. The parity check ensures that if a single cell error converts a token into a different legitimate token, then there will be a parity error so that the processing circuitry in the receiver/stimulator will ignore the transmission.

The table of FIG. 16A lists in the "Original Token" column the 8 allowed tokens, identified by the letters (a)–(h). In the column labelled "Error Affected Token", there are listed all possible legitimate tokens for each possible single error in the original token. Thus, for example, token (a), 111110, can give rise to 6 possible tokens for each of 6 single-cell errors, but only the three tokens shown in FIG. 16A are included in the table of FIG. 12. Of these, the third, 111010 (token No. 9 in the table of FIG. 12), is not used, i.e., it is readily detected as being an error. The other two error results are labelled (f) and (h) since they correspond to these "original" tokens in the left column.

Three of the original tokens, if subjected to a single error, give rise to sync tokens. These are of relatively little concern because the detection of a sync token in the middle of a frame where a sync token should not be present is an indication of an error, and this is sufficient to prevent electrode stimulation for the frame. The real concern is for the transition of one of the original tokens (a)–(h) into another one of these tokens. The matrix of FIG. 16B has a check mark for each transition possibility. For example, original token (f), according to the table of FIG. 16A, can be converted by a single error into token (a) or token (e), so check marks are placed in rows (a) and (e) of the matrix to show that the original token can be converted into either one of two other legitimate tokens if a single error occurs.

It is apparent from the matrix that there is no problem at all with token (c) because a single bit error cannot change it into a legitimate token. As for tokens (a), (b), (d) and (e), a single error results in one of legitimate tokens (f), (g) or (h). Conversely, an error in one of the tokens (f), (g) or (h) gives rise to one of tokens (a),(b), (d) or (e). By assigning the four 3-bit sequences that have odd parity to tokens (a), (b), (d) and (e), shown in FIG. 12 as Nos. 12, 11, 8 and 5, and the four 3-bit sequences that have even parity to tokens (c), (f), (g) and (h), shown in FIG. 12 as Nos. 10, 4, 3 and 7, it is apparent that following the conversion of all tokens in a frame to their corresponding tri-bit sequences, a single error in a frame, i.e., a single change in the bit of a single token, will result in the overall parity of the 3 data tokens and the error token in a data block changing, thereby ensuring detection of all single cell errors in a data block.

Token 101101 (token No. 3 in FIG. 12 and token (g) in FIGS. 16A and 16B) is assigned to the tri-bit sequence 011. In any data block, this is the token used for the parity token if the parity of the data encoded in the 3 data tokens is even. Thus if the nine ultimate data bits $E_5$–$E_1$ and $M_5$–$M_2$ in FIG. 13B (represented by the 3 data tokens in the first data block of a frame) have even parity, than the even parity error token is appended to the data tokens just before the phase extender. This guarantees that when the data block is decoded, the total number of 1s in the 12 decoded bits (9 data and 3 parity) should be even. Similar remarks apply to the second data block in the frame. Conversely, the odd parity error token is used if the parity of the data encoded in the 3 data tokens of a block is odd, once again giving rise to an even number of 1s in the 12 decoded bits. For valid data to have been received, the overall parity of the 12 decoded bits in a data block (decoded from the 3 data tokens and the error token) must be even.

If there is an error in the first data block detected, then the system does not lock onto the frame and continues to look at the incoming data until it finds a Sync Ph1 token together with 3 data tokens and an error token whose 12 decoded bits have even parity. If a valid first data block is detected but after it an incorrect Sync Ph2 token is detected, or the parity of the second decoded data block is incorrect, then the entire frame is discarded.

The link has a high intrinsic degree of error immunity. Even at the greatest inter-coil distance the coils are quite closely coupled for efficient power transfer, and the power level at this close range is quite high and results in an extremely high signal-to-noise ratio and a very low susceptibility to environmental electromagnetic interference. For received data to be validated, an entire valid data frame must be received. The data frame structure is tightly specified, requiring not only alternating Ph1 and Ph2 synchronization tokens at the start of successive data blocks, but also correct error tokens terminating each data block. In each data block there must be 3 legitimate data tokens between the sync and error tokens, and a phase extender of at least one cell must be present at the end of the data block.

There are so many constraints imposed on what is necessary for a valid data frame that it is extremely unlikely that an erroneous frame with valid format and parity checks could occur. If a detectable error does occur, the frame in which it is detected is ignored and no stimulation is applied.

Although the invention has been described with reference to a particular embodiment, it is to be understood that this embodiment is merely illustrative of the application of the principles of the invention. Thus numerous modifications may be made in the illustrative embodiment of the invention and other arrangements may be devised without departing from the spirit and scope of the invention.

We claim:

1. A transmission system comprising an RF transmitter coil; an RF receiver coil in close wireless proximity to said transmitter coil; means for applying to said transmitter coil an RF transmission signal representing a first bit value by N successive cycles of an RF carrier frequency and representing a second bit value by the suppression of RF carrier transmission for M successive cycles; the degree of inter-coil interaction determining the number of cycles of RF carrier frequency induced in said receiver coil in response to the transmission of successive bits of said first value, said inter-coil interaction being affected by inter-coil coupling, inter-coil distance and the Q values of said transmitter and receiver coils; and means for operating on the RF signal induced in said receiver coil to unambiguously determine the number P of transmitted bits of said first value; said operating means including means for counting modulo N, after an initial offset, the number of RF cycles induced in said receiver coil, and said inter-coil interaction being limited to a range that allows a unique number of induced cycles to be counted for each number P of transmitted bits of said first value.

2. A transmission system in accordance with claim 1 wherein at most one bit of said second value is transmitted between bits of said first value.

3. A transmission system in accordance with claim 1 wherein said operating means counts successive RF cycles based upon clock signals derived from the RF carrier transmission.

4. A transmission system in accordance with claim 1 wherein said operating means flags receipt of a bit of said second value when a cycle of the RF signal in said receiver coil falls below a detection threshold.

5. A transmission system in accordance with claim 1 wherein for P successive bits of said first value that follow transmission of a bit of said second value, where P>1, at least (P−1)N+1 RF cycles are counted by said operating means.

6. A transmission system in accordance with claim 1 wherein M=N.

7. A transmission system in accordance with claim 1 wherein, depending upon said inter-coil coupling, said operating means counts a variable number of successive RF cycles for any given number of P successive bits of said first value, and said initial offset is an experimentally determined value.

8. A transmission system in accordance with claim 7 wherein said receiver coil may exhibit ringing for a number of cycles exceeding N, said receiver coil is tuned to a resonant frequency slightly offset from said RF carrier frequency such that during the transmission time for a bit of said second value the phase of the ringing signal in said receiver coil changes significantly from the phase of said RF carrier, and the subsequent receipt of RF cycles representing a bit of said first value causes at least one cycle of the RF signal in said receiver coil to fall below said detection threshold.

9. A transmission system in accordance with claim 7 wherein said receiver coil exhibits an induced oscillation of fewer than N cycles above said detection threshold due to the transmission of N cycles of said RF carrier.

10. A transmission system in accordance with claim 1 wherein said receiver coil may exhibit ringing for a number of cycles exceeding N, said receiver coil is tuned to a resonant frequency slightly offset from said RF carrier frequency such that during the transmission time for a bit of said second value the phase of the ringing signal in said receiver coil changes significantly from the phase of said RF carrier, and the subsequent receipt of RF cycles representing a bit of said first value causes at least one cycle of the RF signal in said receiver coil to fall below said detection threshold.

11. A transmission system in accordance with claim 1 wherein information is transmitted in the form of tokens each of which comprises X bits, each token representing Y data bits where Y<X, and constraints are imposed on allowable sequences of bits in tokens.

12. A transmission system comprising an RF transmitter coil; an RF receiver coil in close wireless proximity to said transmitter coil; means for applying to said transmitter coil an RF transmission signal representing a first bit value by N successive cycles of an RF carrier frequency and representing a second bit value by the suppression of RF carrier transmission for M successive cycles; the degree of inter-coil interaction determining the number of cycles of RF carrier frequency induced in said receiver coil in response to the transmission of successive bits of said first value, said inter-coil interaction being affected by inter-coil coupling, inter-coil distance and the Q values of said transmitter and receiver coils; and means for operating on the RF signal induced in said receiver coil to unambiguously determine the number P of transmitted bits of said first value when the degree of inter-coil interaction is restricted to a predetermined range.

13. A transmission system in accordance with claim 12 wherein M=N.

14. A transmission system in accordance with claim 12 wherein said receiver coil may exhibit ringing for a number of cycles exceeding N, said receiver coil is tuned to a resonant frequency slightly offset from said RF carrier frequency such that during the transmission time for a bit of said second value the phase of the ringing signal in said receiver coil de-synchronizes significantly from said RF carrier, and the subsequent receipt of RF cycles representing a bit of said first value causes at least one cycle of the RF signal in said receiver coil to fall below said threshold value.

15. A transmission system in accordance with claim 12 wherein said receiver coil exhibits an induced oscillation of fewer than N cycles above said threshold value due to the transmission of N cycles of RF carrier.

16. A transmission system in accordance with claim 12 wherein information is transmitted in the form of tokens each of which comprises X bits, each token representing Y data bits where Y<X, and constraints are imposed on allowable sequences of bits in tokens.

17. A transmission system comprising an RF transmitter coil; an RF receiver coil coupled to said RF transmitter coil; means for applying to said RF transmitter coil an RF signal in which a 1 bit is represented by a predetermined number, greater than 2, of cycles of said RF signal and a 0 bit is represented by the absence of a predetermined number, greater than 2, of cycles of said RF signal; the coupling between said coils being such that when the separation of said coils is within prescribed limits the transmission of a single 0 bit between two 1 bits gives rise to at least one RF cycle in said RF receiver coil having an amplitude below a defined percentage of the amplitude of the received RF signal; and means for counting successive RF cycles in said RF receiver coil whose amplitudes exceed said percentage to decode received 0 and 1 bits.

18. A transmission system in accordance with claim 17 wherein said RF transmitter and receiver coils are offset tuned such that, during the transmission of a 0 bit, ringing current in said RF receiver coil changes phase so as to oppose the RF signal received during transmission of the next 1 bit.

19. A transmission system in accordance with claim 18 wherein successive data tokens are transmitted each in the form of X successive bits, with the allowed token values being a subset less than the $2^x$ possible token values and predominantly being those with the fewest 0 bits.

20. A transmission system in accordance with claim 18 wherein said counting means counts a variable number of successive RF cycles for any given number of successive 1 bits and incorporates a counting offset to determine unambiguously the number of successive 1 bits transmitted, said counting means selecting the counting offset according to the extent of the coupling between said coils.

21. A transmission system in accordance with claim 19 wherein the X bits of each data token represent Y data bits, where Y<X, and the Y data bits represented by each data token constitute the information to be communicated by the transmission system.

22. A transmission system comprising an RF transmitter coil; an RF receiver coil coupled to said RF transmitter coil; means for applying to said RF transmitter coil an RF signal in which a 1 bit is represented by a predetermined number, greater than 2, of cycles of said RF signal and a 0 bit is represented by the absence of a predetermined number, greater than 2, of cycles of said RF signal; said RF transmitter and receiver being tuned to slightly different frequencies such that, during the transmission of a 0 bit, any ringing current in said RF receiver coil changes phase so as to oppose the RF signal received during transmission of the next 1 bit giving rise to at least one RF cycle in said RF receiver coil having an amplitude below a defined percentage of the amplitude of the received RF signal; and means for counting successive RF cycles in said RF receiver coil whose amplitudes exceed said percentage to decode received 0 and 1 bits.

23. A transmission system in accordance with claim 22 wherein successive data tokens are transmitted each in the form of X successive bits, with the allowed token values being a subset less than the $2^x$ possible token values and predominately being those with the fewest 0 bits.

24. A transmission system in accordance with claim 22 wherein said counting means counts a variable number of successive RF cycles for any given number of successive 1 bits utilizing a counting offset during the counting to determine unambiguously the number of successive 1 bits transmitted, said counting means selecting the counting offset to be discarded according to the extent of the coupling between said coils.

25. A transmission system in accordance with claim 23 wherein the X bits of each data token represent Y data bits, where Y<X, and the Y data bits represented by each data token constitute the information to be communicated by the transmission system.

26. A method for effecting transmission between an RF transmitter coil and an RF receiver coil variably coupled to said transmitter coil, the inter-coil coupling between said receiver and transmitter coils varying between a predetermined maximum and a predetermined minimum dependent upon the specified range of separation between said coils, comprising the steps of applying to said transmitter coil an RF transmission signal, said RF transmission signal representing a first bit value by N successive cycles of an RF carrier signal and representing a second bit value by the suppression of RF carrier transmission for M successive cycles, and operating on the RF signal induced in said receiver coil by counting with a modulo N counting scheme successive cycles of the RF carrier that exceed a detection threshold and off-setting the count with respect to the start of the successive cycles that are to be counted, said offset being a function of said inter-coil coupling.

27. A method in accordance with claim 26 wherein at most one bit of said second value is transmitted between bits of said first value.

28. A method in accordance with claim 26 wherein in said operating step a bit of said second value is registered when a cycle of the RF signal in said receiver coil falls below a detection threshold.

29. A method in accordance with claim 26 wherein M=N.

30. A method in accordance with claim 26 wherein, depending upon said inter-coil coupling, in said operating step a variable number of successive RF cycles for any given number of successive bits of said first value are counted with a counting offset depending upon said inter-coil coupling to determine unambiguously the number of successive 1 bits transmitted.

31. A method in accordance with claim 26 wherein said receiver coil may exhibit ringing for a number of cycles exceeding N, and further including the step of tuning said receiver coil to a resonant frequency slightly offset from said RF carrier frequency such that during the transmission time for a bit of said second value the ringing signal in said receiver coil falls out of phase significantly from said RF carrier so that the subsequent receipt of RF cycles representing a bit of said first value causes at least one cycle of the RF signal in said receiver coil to fall below said detection threshold.

32. A method in accordance with claim 26 wherein said receiver coil exhibits an induced oscillation of less than N cycles with amplitudes above said detection threshold due to the transmission of N cycles of said RF carrier.

33. A method in accordance with claim 26 wherein information is transmitted in the form of tokens each of which comprises X bits, each token representing Y data bits where Y<X, and constraints are imposed on allowable sequences of bits in tokens.

34. A method in accordance with claim 33 wherein in any token at most one bit of said second value may be transmitted between bits of said first value.

35. A method for effecting transmission between an RF transmitter coil and an RF receiver coil variably coupled to said transmitter coil, damping in said receiver coil varying between a predetermined maximum and a predetermined minimum dependent upon the specified range of separation between said coils, comprising the steps of applying to said transmitter coil an RF carrier signal, said RF carrier signal representing a first bit value by N successive cycles and representing a second bit value by the suppression of RF carrier transmission for M successive cycles; and operating on the RF signal induced in said receiver coil by counting modulo N, with a counting offset depending on the degree of inter-coil coupling, successive cycles of the RF carrier signal in the coil that exceed a threshold value.

36. A method in accordance with claim 35 wherein N and M have values related to the characteristics of said coils and the coupling between said coils is limited to a range such that while a variable number of successive RF cycles may be counted for any given number of successive bits of said first value, the number of successive received bits of said first value may be determined unambiguously.

37. A method in accordance with claim 35 wherein for P successive bits of said first value that follow transmission of a bit of said second value, where P>1, at least (P−1)N+1 RF cycles are counted.

38. A method in accordance with claim 35 wherein M=N.

39. A method for effecting transmission between an RF transmitter coil and an RF receiver coil coupled to said RF transmitter coil comprising the steps of applying to said RF transmitter coil an RF signal in which a 1 bit is represented by a predetermined number, greater than 2, of cycles of said RF signal and a 0 bit is represented by the absence of a predetermined number, greater than 2, of cycles of said RF signal; establishing the coupling between said coils such that when the separation of said coils is within prescribed limits the transmission of a single 0 bit between two 1 bits gives rise to at least one RF cycle in said RF receiver coil having an amplitude below a defined percentage of the amplitude of the received RF signal; and counting successive RF cycles in said RF receiver coil whose amplitudes exceed said percentage to decode received 0 and 1 bits.

40. A method in accordance with claim 39 wherein said RF transmitter and receiver coils are tuned at slightly different frequencies such that, during the transmission of a 0 bit, ringing current in said RF receiver coil changes phase so as to oppose the RF signal received for the next 1 bit.

41. A method in accordance with claim 40 wherein a variable number of successive RF cycles are counted for any given number of successive 1 bits, said counting commencing with a counting offset that is dependent upon said intercoil coupling, to determine unambiguously the number of successive 1 bits transmitted.

42. A method in accordance with claim 40 wherein successive data tokens are transmitted each in the form of X successive bits, with the allowed token values being a subset less than the $2^x$ possible token values and predominately being those with the fewest 0 bits.

43. A method in accordance with claim 42 wherein the X bits of each data token represent Y data bits, where Y<X, and the Y data bits represented by each data token constitute the information to be communicated by the transmission system.

44. A method for effecting transmission between an RF transmitter coil and an RF receiver coil coupled to said RF transmitter coil comprising the steps of applying to said RF transmitter coil an RF signal in which a 1 bit is represented by a predetermined number, greater than 2, of cycles of said RF signal, and a 0 bit is represented by the absence of a predetermined number, greater than 2, of cycles of said RF signal; slightly offsetting the tuning of said RF transmitter and receiver coils such that, during the transmission of a 0 bit, ringing current in said RF receiver coil changes phase so as to oppose the RF signal received for the next 1 bit giving rise to at least one RF cycle in said RF receiver coil having an amplitude below a defined percentage of the amplitude of the received RF signal; and counting successive RF cycles in said RF receiver coil whose amplitudes exceed said percentage to decode received 0 and 1 bits.

45. A method in accordance with claim 44 wherein successive data tokens are transmitted each in the form of X successive bits, with the allowed token values being a subset less than the $2^x$ possible token values and predominately being those with the fewest 0 bits.

46. A method in accordance with claim 44 wherein a variable number of successive RF cycles are counted for any given number of P successive 1 bits, said counting commencing with a counting offset that is dependent upon said inter-coil coupling, to determine unambiguously the number P.

47. A method in accordance with claim 45 wherein the X bits of each data token represent Y data bits, where Y<X, and the Y data bits represented by each data token constitute the information to be communicated by the transmission system.

48. A transmission system comprising an RF transmitter coil; an RF receiver coil in close wireless proximity to said transmitter coil; means for applying to said transmitter coil an RF transmission signal representing a first bit value by N successive cycles of an RF carrier frequency and representing a second bit value by the suppression of RF carrier transmission for M successive cycles; the degree of inter-coil interaction determining the number of cycles of RF carrier frequency induced in said receiver coil in response to the transmission of successive bits of said first value, said inter-coil interaction being affected by inter-coil coupling, inter-coil distance and the Q values of said transmitter and receiver coils; and means for operating on the RF signal induced in said receiver coil to unambiguously determine the number P of bits of said first value transmitted when the degree of inter-coil interaction is restricted to a predetermined range [R',R*−1], where R*=R'+N and R' is the lowest value of R calculated by R=K−N(P−1) determined by experimentation for preset N and P with variable inter-coil interaction, and K is a count of the number of RF carrier frequency cycles induced in the receiver coil exceeding a detection threshold so that P is determined to be a unique integer satisfying $(K+1−R')/N \leq P \leq (K−R')/N+1$.

49. A transmission system in accordance with claim 48 wherein for P successive bits of said first value that follow transmission of a bit of said second value, where P>1, K is a unique integer satisfying $N(P−1)+R' \leq K \leq NP+R'−1$.

50. A transmission system in accordance with claim 48 wherein, depending upon said inter-coil coupling, said operating means counts a variable number of successive RF cycles for any given number of successive bits of said first value and ignores a variable number of counted cycles depending upon said inter-coil coupling to determine unambiguously the number of successive transmitted bits of said first value.

51. A transmission system comprising an RF transmitter coil; an RF receiver coil in close wireless proximity to said transmitter coil; means for applying to said transmitter coil an RF transmission signal representing a first bit value by N successive cycles of an RF carrier frequency and representing a second bit value by the suppression of RF carrier transmission for M successive cycles; the degree of inter-coil interaction determining the number of cycles of RF carrier frequency induced in said receiver coil in response to the transmission of successive bits of said first value, said inter-coil interaction being affected by inter-coil coupling, inter-coil distance and the Q values of said transmitter and receiver coils; and means for operating on the RF signal induced in said receiver coil to unambiguously determine the number P of bits of said first value when the degree of inter-coil interaction is restricted to a predetermined range [R',R*−1], where R*=R'+N and R' is the minimum of a plurality of values of R calculated by R=K−N(P−1) determined by experimentation for preset N and P over a range of several inter-coil interactions, said operating means performing each calculation by (i) discarding the first R'−1 cycles of the K successive RF cycles induced in said receiver coil, (ii) counting modulo N all remaining cycles of the successive RF cycles, and (iii) determining the number P by generating a flagging event on every modulo N count of 1.

52. A cochlear implant system comprising:

a wearable speech processor for receiving ambient sounds and generating in response a plurality of sequential stimulation signals, each said stimulation signal having a duration, said processor including a transmitter for transmitting said sequential stimulation signals; and an implantable cochlear stimulator, said stimulator including a receiver for receiving said stimulation signals and a plurality of electrodes for applying said stimulation signals to a patient's aural nerve, each stimulation signal being applied for the corresponding duration for said stimulation signal;

wherein said transmitter transmits said sequential stimulation signals as a stream of digital data partitioned into frames, each frame corresponding to one of said stimulation signals, each said frame including data defining characteristics of a following stimulation signal except for the duration of said following stimulation signal, each frame having a frame duration which defines the duration of the current stimulation signal.

53. A cochlear implant system comprising:

an internal stimulator having a receiver, and a plurality of electrodes for applying stimulation to the patient's aural nerve; and an external speech processor for receiving ambient sounds and for generating in response a plurality of processed signals, each processed signal including data defining a duration and at least one other characteristic of a corresponding stimulation signal, said processor including a transmitter for transmitting a sequence of data frames corresponding to each said processed signal, each frame including frame data defining said other characteristic and a frame duration defining the duration of the current stimulation signal.

54. The system of claim 53 wherein said plurality of electrodes are arranged in electrode pairs, and wherein said one characteristic includes a designation of one of said electrode pairs.

55. The system of claim 53 wherein each stimulation signal is defined by an amplitude, a starting electrode and a stimulation mode.

56. The system of claim 53 wherein each frame includes data defining at least one characteristic of the immediately following stimulation signal.

57. The system of claim 53 wherein
said sequence of data frames includes consecutive first and second frames corresponding to consecutive first and second signals wherein said second frame includes data defining at least said one characteristic of said first signal and has a second frame duration which defines the duration of said first signal.

58. A system comprising an RF transmitter and an RF receiver, said transmitter and said receiver both operating on frames having a predetermined format and representing both digital data and time-interval information; said RF transmitter including means for selectively generating and suppressing RF carrier cycles to represent digital data and to do so within a frame for an overall variable period representative of time-interval information, the RF carrier cycles representative of said digital data being embedded within the overall RF transmission representative of said time-interval information; and said RF receiver including means for detecting individual carrier cycles in the received RF transmission, means for decoding individually detected carrier cycles to derive digital data, and means for deriving time-interval information from the period required to detect all carrier cycles in the current frame.

59. A system in accordance with claim 58 further including means responsive to digital data and time-interval information derived by said RF receiver for generating an output that is a function of both, each generated output being a function of the time interval information represented in the current frame and the digital data represented in the preceding frame.

60. A system in accordance with claim 59 wherein said output generating means is a cochlear implant, and said RF transmitter and RF receiver are spaced apart by a distance characteristic of a cochlear implant system.

61. A system in accordance with claim 60 wherein said RF transmitter includes a coil and said RF receiver includes a coil variably coupled to said transmitter coil, the extent of nulling of any ringing signal in said receiver coil due to presently transmitted RF cycles varying between a predetermined maximum and a predetermined minimum dependent upon the specified range of separation between said coils; said generating and suppressing means applies to said transmitter coil an RF transmission signal representing a first bit value by N successive cycles of an RF carrier frequency and representing a second bit value by the suppression of RF carrier transmission for M successive cycles; and said RF receiver detecting means operates on the RF signal induced in said receiver coil to unambiguously determine the number P of bits of said first value when the degree of inter-coil interaction is restricted to a predetermined range.

62. A system in accordance with claim 61 wherein at most one bit of said second value is transmitted between bits of said first value.

63. A system in accordance with claim 61 wherein said detecting means counts successive RF cycles based upon clock signals derived from the RF carrier transmission.

64. A system in accordance with claim 61 wherein said detecting means flags receipt of a bit of said second value when a cycle of the RF signal in said receiver coil falls below a detection threshold.

65. A system in accordance with claim 61 wherein, depending on the separation between said coils, said detecting means counts a variable number of successive RF cycles as being indicative of any given number of successive bits of said first value.

66. A system in accordance with claim 65 wherein said receiver coil may exhibit ringing for a number of cycles exceeding N, said receiver coil is tuned to a resonant frequency slightly offset from said RF carrier frequency such that during the transmission time for a bit of said second value the ringing signal in said receiver coil falls out of phase significantly from said RF carrier, and the subsequent receipt of RF cycles representing a bit of said first value causes at least one cycle of the RF signal in said receiver coil to fall below said detection threshold.

67. A system in accordance with claim 61 wherein said receiver coil may exhibit ringing for a number of cycles exceeding N, said receiver coil is tuned to a resonant frequency such that during the transmission time for a bit of said second value the ringing signal in said receiver coil changes in phase significantly from said RF carrier, and the subsequent receipt of RF cycles representing a bit of said first value causes at least one cycle of the RF signal in said receiver could to fall below said detection threshold.

68. A system in accordance with claim 61 wherein said digital data is transmitted in the form of tokens each of which comprises X bits, each token representing Y data bits where Y<X, and constraints are imposed on allowable sequences of bits in tokens.

69. A system in accordance with claim 68 wherein in any token at most one bit of said second value may be transmitted between bits of said first value.

70. A transmitter for transmitting variable-duration frames having a predetermined format and representing both digital data and time-interval information comprising means for selectively generating and suppressing RF carrier cycles to represent digital data, and means for transmitting the generated RF carrier cycles within a frame for a period representative of time-interval information, the RF carrier cycles representative of said digital data being embedded within the overall RF transmission representative of said time-interval information.

71. A method of transmitting successive frames, each frame having both analog and digital command information for selected utilization circuits, comprising the steps of transmitting in each frame the analog command information for a first respective utilization circuit and transmitting in each frame the digital command information for a second respective utilization circuit, wherein said second utilization circuit operates on the digital command information conveyed in the previous frame.

72. A method for effecting transmission between an RF transmitter and an RF receiver, said transmitter and said receiver both operating on frames having a predetermined format and representing both digital data and time-interval information, comprising the steps of controlling said RF transmitter to selectively generate and suppress RF carrier cycles to represent digital data and to do so within a frame for an overall variable duration representative of time-interval information, the RF carrier cycles representative of said digital data being embedded within the overall RF transmission representative of said time-interval information; and detecting in said RF receiver individual carrier cycles in the received RF transmission, decoding individually detected carrier cycles to derive digital data, and deriving time-interval information from the period required to detect all carrier cycles in the current frame.

73. A transmission system in accordance with claim 51 wherein for P successive bits of said first value that follow transmission of a bit of said secured value where P>1, K is a unique integer satisfying $N(P-1)30 \ R' \leq K \leq NP+R'-1$.

* * * * *